United States Patent
Kishida et al.

(10) Patent No.: US 10,028,667 B2
(45) Date of Patent: Jul. 24, 2018

(54) FIBER OPTIC IN VIVO DIAGNOSTIC SENSOR SYSTEM AND BLOOD VESSEL INSERTABLE PRESSURE DISTRIBUTION MEASUREMENT DEVICE

(71) Applicant: NEUBREX CO., LTD., Kobe-shi, Hyogo (JP)

(72) Inventors: Kinzo Kishida, Kobe (JP); Yoshiaki Yamauchi, Kobe (JP)

(73) Assignee: NEUBREX CO., LTD., Kobe-Shi, Hyogo (JP)

( * ) Notice: Subject to any disclaimer, the term of this patent is extended or adjusted under 35 U.S.C. 154(b) by 0 days.

(21) Appl. No.: 15/022,016

(22) PCT Filed: Jul. 25, 2014

(86) PCT No.: PCT/JP2014/069685
§ 371 (c)(1),
(2) Date: Mar. 15, 2016

(87) PCT Pub. No.: WO2015/059969
PCT Pub. Date: Apr. 30, 2015

(65) Prior Publication Data
US 2016/0220131 A1 Aug. 4, 2016

(30) Foreign Application Priority Data
Oct. 25, 2013 (JP) .................... 2013-221766

(51) Int. Cl.
*A61B 5/0215* (2006.01)
*A61B 5/1459* (2006.01)
(Continued)

(52) U.S. Cl.
CPC .......... *A61B 5/02154* (2013.01); *A61B 5/015* (2013.01); *A61B 5/1459* (2013.01);
(Continued)

(58) Field of Classification Search
CPC ............. A61B 1/00165; A61B 5/0215; A61B 5/02154; A61B 5/0261
(Continued)

(56) References Cited

U.S. PATENT DOCUMENTS

| 5,107,847 A | 4/1992 | Knute et al. |
| 5,684,297 A | 11/1997 | Tardy |

(Continued)

FOREIGN PATENT DOCUMENTS

| CN | 1183548 A | 6/1998 |
| CN | 102162757 A | 8/2011 |

(Continued)

OTHER PUBLICATIONS

Office Action (Notification of Reason for Refusal) dated Jan. 31, 2017, by the Japanese Patent Office in corresponding Japanese Patent Application No. 2015-543732 and English translation of the Office Action. (9 pages).

(Continued)

*Primary Examiner* — Allen Porter, Jr.
(74) *Attorney, Agent, or Firm* — Buchanan Ingersoll & Rooney PC

(57) ABSTRACT

A fiber optic biodiagnostic sensor system includes a blood vessel insertable pressure distribution measurement device to be inserted in vivo into a blood vessel to measure distributions of temperature and pressure of an object to be measured along a predetermined site, the device having an SM optical fiber deformable by temperature and strain, a structural member being in contact with a portion of the optical fiber to convert pressure of the to-be-measured object to strain of the optical fiber; and an outer layer converting the optical fiber and the structural member. The sensor system further includes a measurement unit emitting laser light into the SM optical fiber, detecting a frequency shift (Continued)

produced in the scattered light, and calculating a blood pressure at a given position of the optical fiber from a pressure change and a strain change of the SM optical fiber that are calculated from the frequency shift.

7 Claims, 18 Drawing Sheets

(51) Int. Cl.

| | | |
|---|---|---|
| G01L 1/24 | (2006.01) | |
| G01D 5/353 | (2006.01) | |
| G01K 11/32 | (2006.01) | |
| G01K 13/00 | (2006.01) | |
| A61B 5/00 | (2006.01) | |
| A61B 5/01 | (2006.01) | |
| A61B 90/30 | (2016.01) | |
| A61B 5/0205 | (2006.01) | |

(52) U.S. Cl.
CPC ............. *A61B 5/72* (2013.01); *A61B 5/7278* (2013.01); *G01D 5/35361* (2013.01); *G01D 5/35364* (2013.01); *G01K 11/32* (2013.01); *G01K 13/002* (2013.01); *G01L 1/242* (2013.01); *G01L 1/247* (2013.01); *A61B 5/02055* (2013.01); *A61B 5/742* (2013.01); *A61B 2090/306* (2016.02); *A61B 2560/0475* (2013.01)

(58) Field of Classification Search
USPC ....... 600/462, 465, 468, 472, 478, 479, 480, 600/485
See application file for complete search history.

(56) References Cited

U.S. PATENT DOCUMENTS

| | | |
|---|---|---|
| 2009/0185772 A1 | 7/2009 | Xia et al. |
| 2009/0289808 A1 | 11/2009 | Prammer |
| 2009/0306650 A1 | 12/2009 | Govari et al. |
| 2011/0098533 A1 | 4/2011 | Onoda et al. |
| 2011/0098579 A1* | 4/2011 | Ajiki .................. A61B 5/02154 600/485 |
| 2011/0137140 A1 | 6/2011 | Tearney et al. |
| 2011/0238020 A1 | 9/2011 | Goedje et al. |
| 2012/0176138 A1 | 7/2012 | Prammer |
| 2012/0197097 A1 | 8/2012 | Chan et al. |
| 2012/0274477 A1 | 11/2012 | Prammer |
| 2013/0131489 A1 | 5/2013 | Govari et al. |
| 2013/0131663 A1 | 5/2013 | Govari et al. |
| 2014/0012251 A1 | 1/2014 | Himmelstein et al. |
| 2014/0058275 A1* | 2/2014 | Gregorich .......... A61B 5/02141 600/485 |
| 2014/0180030 A1* | 6/2014 | Dorando ................ A61B 5/026 600/301 |
| 2014/0243688 A1 | 8/2014 | Caron et al. |
| 2014/0246237 A1 | 9/2014 | Prammer |
| 2014/0249386 A1 | 9/2014 | Caron et al. |
| 2015/0204187 A1 | 7/2015 | Prammer |
| 2015/0337651 A1 | 11/2015 | Prammer |
| 2016/0022159 A1 | 1/2016 | Caron et al. |
| 2016/0074112 A1 | 3/2016 | Himmelstein et al. |
| 2016/0116308 A1* | 4/2016 | Xue ..................... G01L 1/242 385/12 |
| 2016/0128583 A1 | 5/2016 | Caron et al. |
| 2016/0262829 A1 | 9/2016 | Govari et al. |
| 2016/0326867 A1 | 11/2016 | Prammer |
| 2017/0027458 A1 | 2/2017 | Glover et al. |

FOREIGN PATENT DOCUMENTS

| | | |
|---|---|---|
| EP | 0 127 476 A2 | 12/1984 |
| EP | 2130508 A2 | 12/2009 |
| GB | 2 308 888 A | 7/1997 |
| JP | 8-240451 A | 9/1996 |
| JP | 2004-170168 A | 6/2004 |
| JP | 2010-216877 A | 9/2010 |
| JP | 2012-533353 A | 12/2012 |
| WO | WO 2010/050526 A1 | 5/2010 |
| WO | WO 2011/048509 A1 | 4/2011 |
| WO | 2012/122157 A1 | 9/2012 |
| WO | 2013/061280 A1 | 5/2013 |
| WO | WO 2013/061281 A1 | 5/2013 |

OTHER PUBLICATIONS

International Search Report (PCT/ISA/210) dated Oct. 7, 2014, by the Japanese Patent Office as the International Searching Authority for International Application No. PCT/JP2014/069685.
Written Opinion (PCT/ISA/237) dated Oct. 7, 2014, by the Japanese Patent Office as the International Searching Authority for International Application No. PCT/JP2014/069685.
Stephen Kreger et al., "High-resolution distributed fiber-optic sensing for dynamic structural monitoring" SPIE Newsroom, Jun. 14, 2013, DOI: 10.1117/2.1201305.004826; 3 pages.
Robert O. Bonow et.al, "Braunwald's Heart Disease: A Textbook of Cardiovascular Medicine" Ninth Edition, Elsevier Saunders, 2012; pp. 383-405.
"JSME Mechanical Engineers' Handbook", β8: Bioengineering, pp. 65-75, edit. The Japan Society of Mechanical Engineers, 2007; pp. 65-75.
Chinese Office Action ("First Office Action") dated Apr. 21, 2017, by the Chinese Patent Office in corresponding Chinese Patent Application No. 201480058654.8 and English translation of the Office Action (14 pages).
Extended European Search Report dated Jun. 8, 2017, issued by the European Patent Office in corresponding European Application No. 14855749.9. (8 pages).
Office Action (The Second Office Action) dated Dec. 5, 2017, by the State Intellectual Property Office of the People's Republic of China in corresponding Chinese Patent Application No. 201480058654.8, and an English Translation of the Office Action. (21 pages).
Chinese Office Action ("Third Office Action") dated May 11, 2018, by the Chinese Patent Office in corresponding Chinese Patent Application No. 201480058654.8 and English translation of the Office Action (14 pages).
Communication pursuant to Article 94(3) EPC dated May 22, 2018 by the European Patent Office in corresponding European Patent Application No. 14 855 749.9 (5 pages).

\* cited by examiner

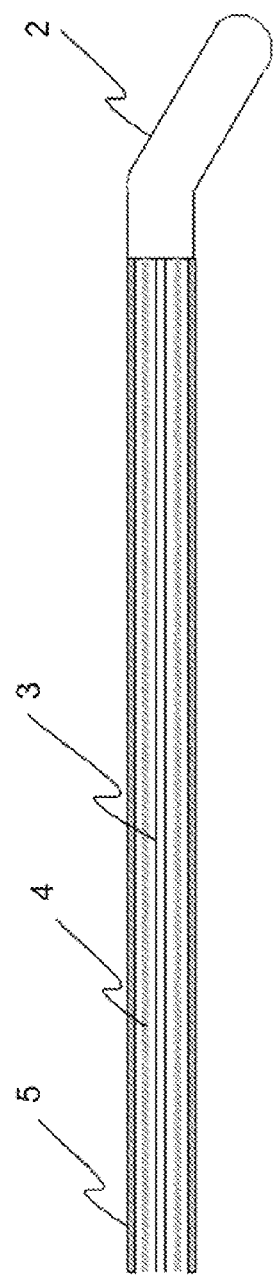
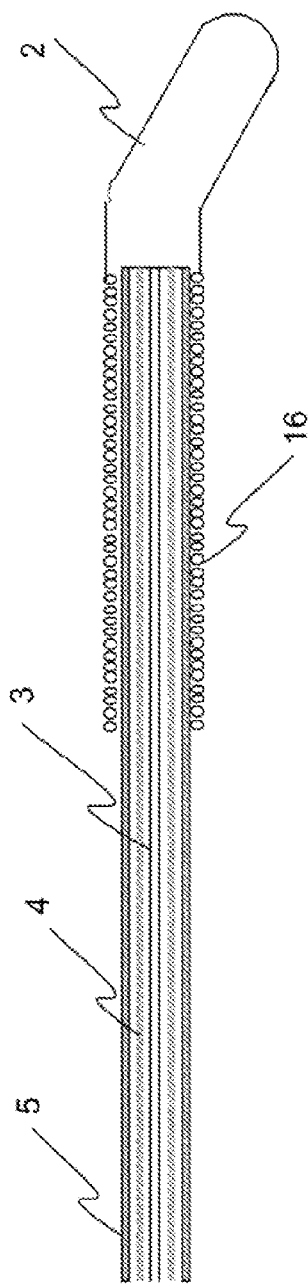

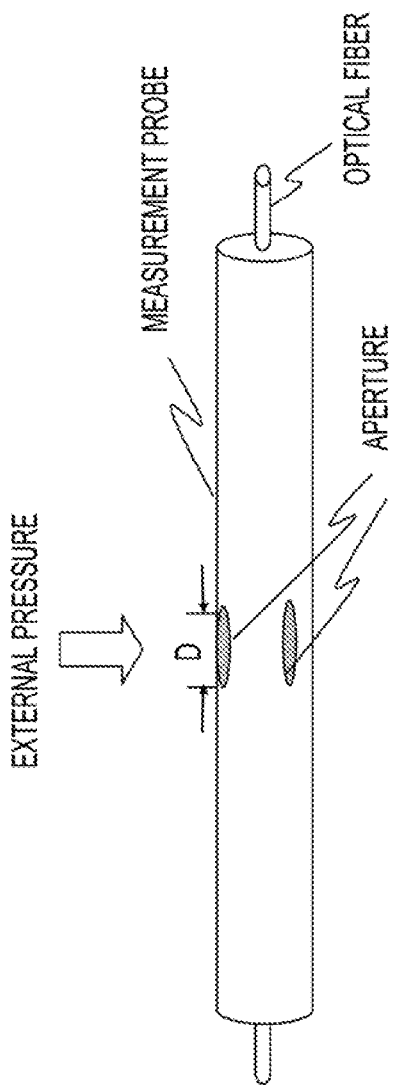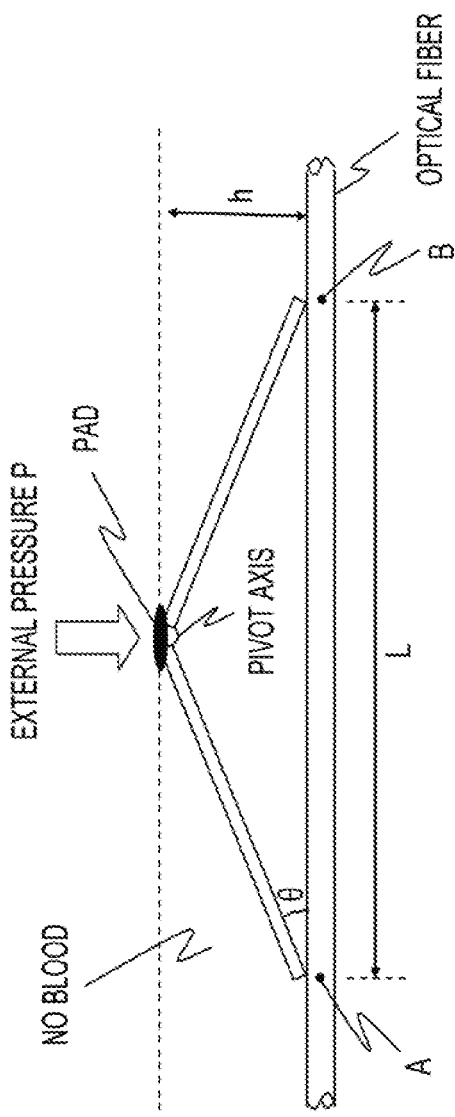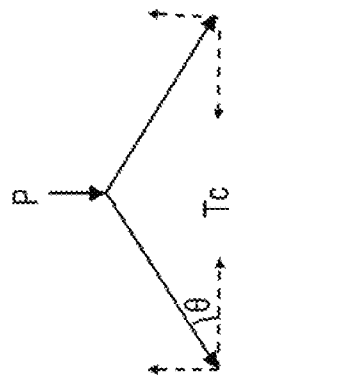

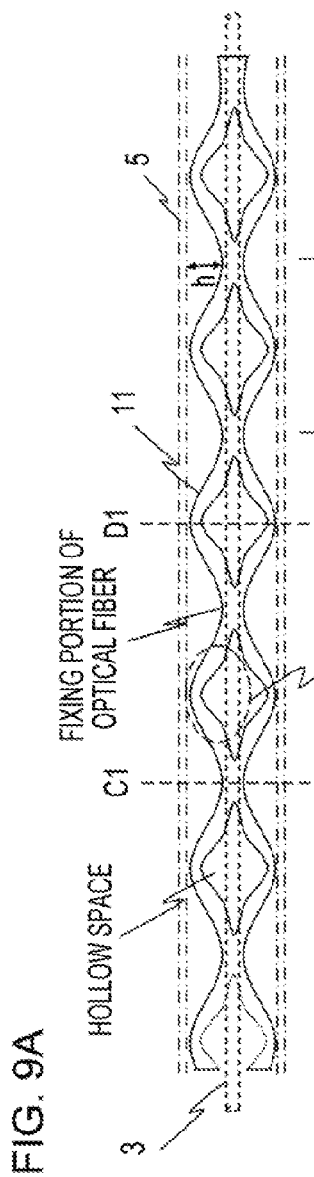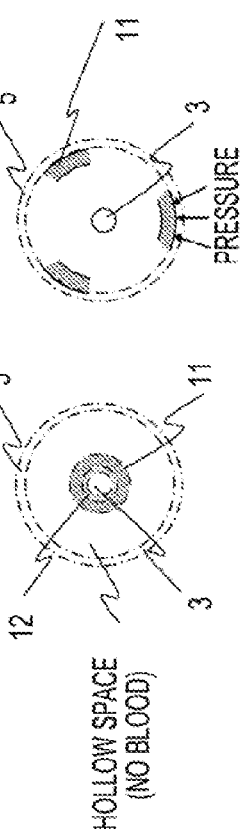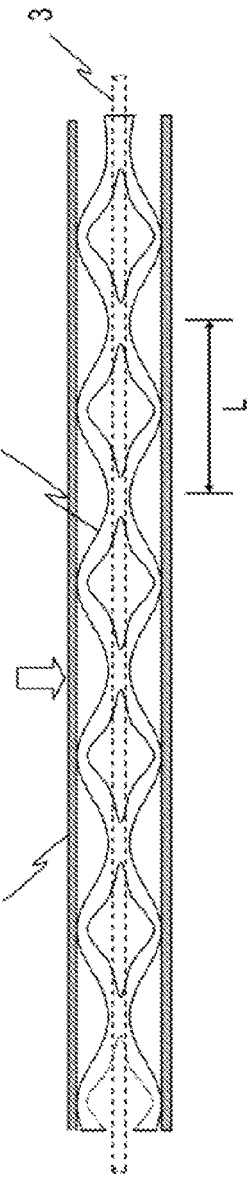

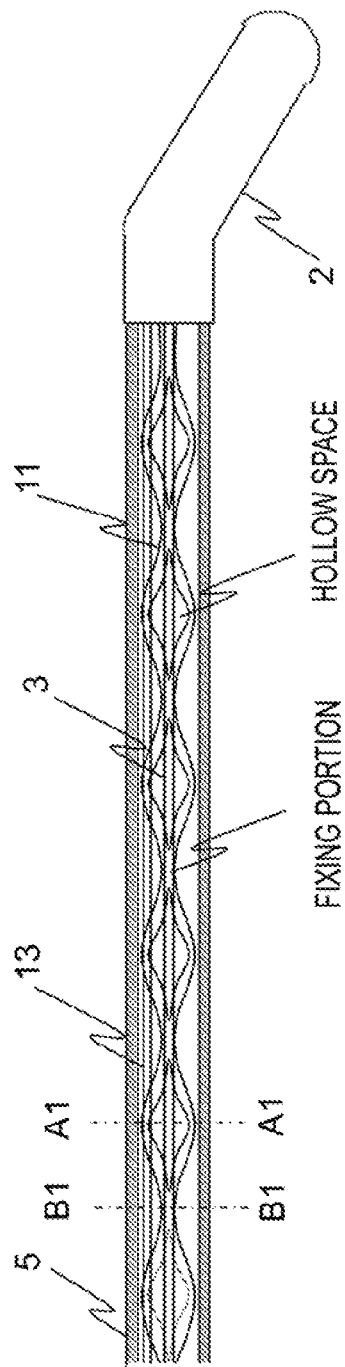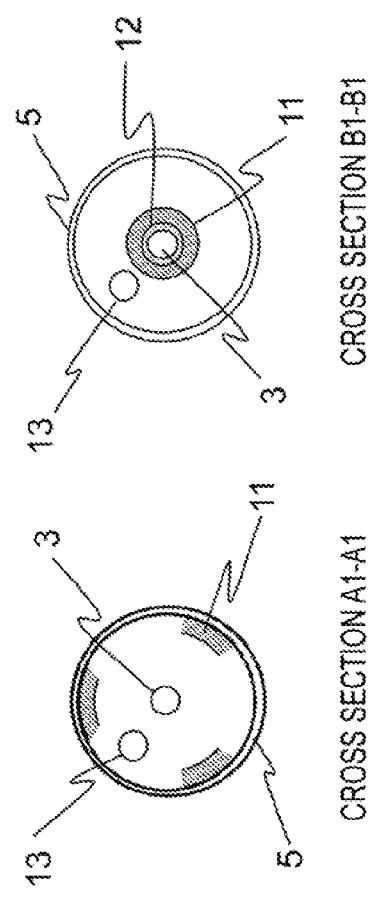

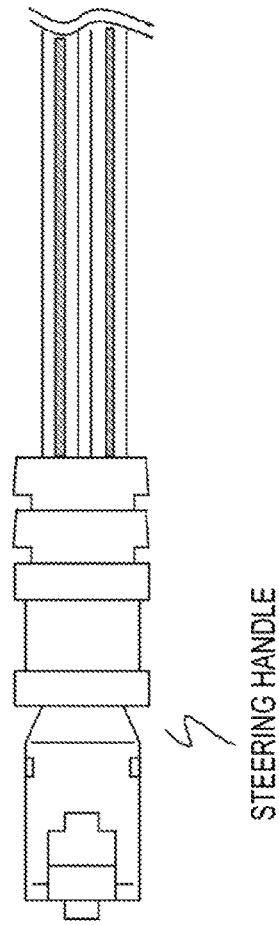
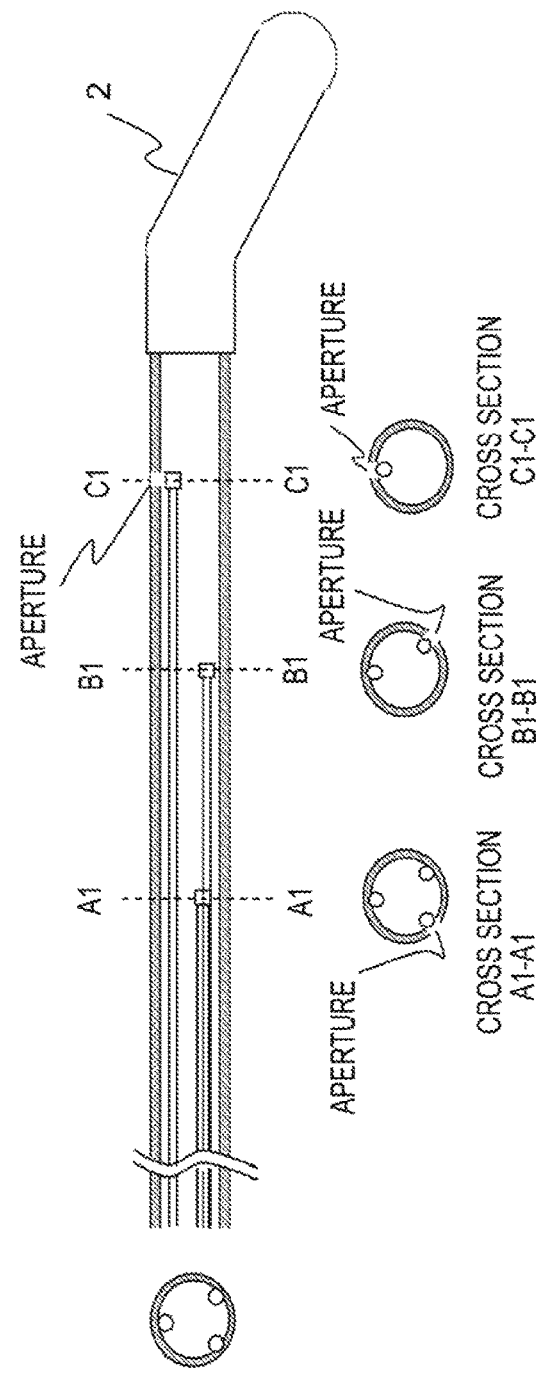
FIG. 18 PRIOR ART

FIBER OPTIC IN VIVO DIAGNOSTIC SENSOR SYSTEM AND BLOOD VESSEL INSERTABLE PRESSURE DISTRIBUTION MEASUREMENT DEVICE

TECHNICAL FIELD

The present invention relates to medical measurement systems, and more particularly relates to a fiber optic in vivo diagnostic sensor system that uses a distributed optical fiber sensor system for measuring distributions of temperature, pressure, and strain by means of an optical fiber to provide in vivo diagnostic information by acquiring and analyzing in vivo information such as blood pressure, and relates to a blood vessel insertable pressure distribution measurement device for measuring blood pressure and the like.

BACKGROUND ART

Conventionally, in measurement of pressure or flow rate in a percutaneous transluminal coronary angioplasty (PCI), the fractional flow reserve (FFR) is used as an important diagnostic index. The PCI is a treatment method for ischemic heart disease. The method increases the blood flow rate by dilating the cardiac coronary artery stenosed such as by an atheroma (a deposit or plaque inside an arterial vessel that are formed of cells or dead cells containing fatty substances, calcium and various fibrillary connections). The FFR index indicates the degree of blood flow constriction due to a stenotic lesion and is expressed as a ratio of a blood flow rate at a portion distal to the stenotic lesion site to a normal blood flow rate there. Specifically, a pressure $P_a$ in the aorta proximal to a stenotic lesion site and a pressure $P_d$ in a coronary artery distal thereto are measured, to calculate the FFR index from $P_d/P_a$. This will be explained in a little more detail with reference to FIGS. 6A and 6B. FIG. 6A is a schematic diagram showing stenotic lesions produced in a blood vessel, wherein the arrows indicate the blood flow direction. FIG. 6B is a model diagram of a pressure change in the blood vessel corresponding to FIG. 6A. In FIG. 6B, the vertical axis represents a maximum pulse pressure in the blood vessel and the horizontal axis represents an optical fiber length $L_{of}$. The optical fiber length here is the distance from a given start point, which is defined as zero, of the optical fiber to the distal end of the sensor. Designating stenosis positions of a lesion site Pc1 and a lesion site Pc2 at S1 and S2, respectively, the pressures in the blood vessel (blood pressures) along these sites gradually decrease from a reference pressure $P_0$ (corresponding to the above described pressure $P_a$) as shown in the figure. And expressing pressures gradually decreased at the stenosis positions S1 and S2 by $P_1$ and $P_2$, respectively, $P_1/P_0$ and $P_2/P_0$ are called the fractional flow reserves (FFRs) at the respective positions. When either value of the FFRs is less than 0.75, the above-described PCI is applied. Ordinarily, the pressure $P_a$ is measured at the head of a guiding catheter and the pressure $P_d$ is measured with a pressure sensor at the head of a dedicated catheter called a pressure wire. In order to diagnose a symptom such as due to not a single stenosis but multiple stenoses or a physiological state that is information after a stent is placed, blood pressure or velocity is demanded in the PCI to be measured not as one point value but as a distribution.

In more detail, taking into account the size of a heart valve and the longitudinal size of a coronary artery stenosis, resolution of about 3 mm to 5 mm is desired in measurement such as of a longitudinal pressure distribution. The finer the diameter (for example, less than 0.4 mm) of a measurement probe, the better for insertion into a small coronary artery and through a heart valve, and a probe suitable for the measurement needs to have an appropriate stiffness and an optical fiber supporting mechanism. Considering the above, it is difficult for a probe to satisfy a specification of 0.4 mm or less for the outer diameter when a plurality of optical fibers are used in order to achieve the present measurement purpose. Moreover, in order to be able to measure temperature, velocity and the like simultaneously in addition to pressure measurement of a diseased site and to perform the measurement without affecting heartbeat, a multifunctional sensor without using an electrosensor is requested.

Conventionally, there has been a fiber Bragg grating (FBG) sensor as an optical fiber sensor used for such a purpose. However, the sensor needs formation of an FBG in the fiber. The original function of the sensor is temperature measurement through stretch or thermal deformation of the optical fiber, and it is difficult to particularly measure only pressure itself. In addition to the proposal so far, a pressure conversion mechanism is necessarily provided at a section where the FBG senses pressure. Thus, spatially continuous pressure cannot be measured. Moreover, a plurality (three or more) of fibers are needed to satisfy a specification of multifunctionality (multi-measurement function) capable of measuring quantities other than pressure, thus posing a hurdle to meet requirement of finer diameter (see, for example, Patent Document 1). Furthermore, since there is no sensor-functional section between FBGs, it is essentially difficult to measure a spatially continuous signal (see, for example, Non-Patent Document 1).

Although a quick multipoint measurement of temperature and pressure and a measurement of multi-parameters is enabled by coating an FBG portion with Zn metal vapor or the like, the sensor sensitivity is insufficient. Furthermore, while shape change of a measurement fiber incorporated catheter used for medical purposes causes strain in the measurement fiber, the frequency change by the strain is larger than that by pressure, thus posing difficulty in distinguishing a pressure signal from a strain signal.

There has been a sensor system that employs a single probe to improve the above problems. The sensor system is for measuring pressure and a flow rate by use of four microelectromechanical optical sensors (MEMS). Since apertures for pressure measurement are necessarily formed in the probe surface at positions corresponding to attached positions of the sensors, the measurement is limited to only several points located at certain intervals, thus posing a major obstacle in actual use. Moreover, need of a plurality of optical sensors is disadvantageous for making the probe finer.

Furthermore, since the sensors have such a complicated structure as shown in FIG. 18 that a plurality of apertures are necessarily formed in the probe surface at pressure sensing positions (see the cross sections A1-A1, B1-B1, and C1-C1 in FIG. 18), use of the sensors includes a problems from a safety viewpoint. Still further, when an electrosensor, which is another kind of sensor, is concurrently used for multifunctionality, influence to the heart and lungs must be taken into consideration (see, for example, Patent Document 2).

Addition to the above, the conventional technology further raises the following general problems in measurement of pressure and the like in a blood vessel. The first point is that since the sensor is not for a distributed measurement but for a point measurement, the measurement points are finite and restricted by the number of sensors. The second point is that since the measurement needs a plurality of sensors and measurement points are limited to several points as described above, the blood vessel length where the pressure and the like can be measured without moving the probe is shorted. The third point is that since a plurality of sensors are needed, the probe cannot be formed to have a diameter finer than a certain level; and the measurement is difficult for a vascular stenosis having a plurality of lesion sites such as because the probe has a complicated structure. The fourth point is that use of a plurality of fibers having different sensitivities fundamentally involves an influence due to the variations in sensor sensitivity; and since the variations in sensor sensitivity needs all products of the sensors to be calibrated though the sensor are thrown away after used temporarily, the sensors do not lend themselves to mass production and wasteful. From these points, it is conceivable that conventional sensors are practically difficult to use as a sensor for measuring pressure and the like in a blood vessel.

PRIOR ART DOCUMENT

Patent Document

Patent Document 1: WO2011/048509 A1
Patent Document 2: WO2013/061281 A1
Patent Document 3: JP2010-216877 A Non-Patent Document Non-Patent Document 1: Stephen Kreger, Alex Sang, Naman Grag and Julia Michel, "High-resolution distributed fiber-optic sensing for dynamic structural monitoring" SPIE Newsroom, 14 Jun. 2013, DOI: 10.1117/2.1201305.004826;
Non-Patent Document 2: Robert O. Bonow et. al, "Braunwald's Heart Disease: A Textbook of Cardiovascular Medicine" ninth edition, ELSEVIER SAUNDERS, 2012; and
Non-Patent Document 3: "JSME Mechanical Engineers' Handbook", ß8: Bioengineering, pp. 65-75, edit. The Japan Society of Mechanical Engineers, 2007.

SUMMARY OF THE INVENTION

Problem that the Invention is to Solve

As described above, implementation of a desired measurement (for example, a fractional flow reserve (FFR) measurement) in a PCI needs a plurality of multifunctional fibers. While capability of separating pressure is needed in the measurement, since the strain sensitivity of an inorganic glass based optical fiber is an order of magnitude larger than the pressure sensitivity thereof in pressure measurement using such the above-described conventional technology, pressure cannot be directly measured because of a large error due to the sensitivity differences. Although use of a plurality of sensors allows for multi-point measurement, difficulty in spatially continuous measurement causes loss of data to be acquired and there are variations in sensor sensitivity among the plurality of sensors. This may lead to inaccurate determination of pathological conditions. Furthermore, since the FBG is artificially formed in the optical fiber, a function inherent to optical fibers, such as a sensing function, may not be utilized in some cases.

In contrast to such the above-described conventional technology, a measurement method has been known in which, by using an optical fiber as a sensor, two or more physical quantities, such as pressure and stain, of an object to be measured are simultaneously separated into independent measurement parameters to measure their distributions. The measurement method uses an optical fiber as a sensor to utilize frequency shifts and/or phase shifts of Brillouin and Rayleigh scattering responsive to various physical quantities such as strain, temperature, and pressure (see, for example, Patent Document 3). Furthermore, there is a measurement method that utilizes an optical fiber characteristic responsive simultaneously to strain, temperature, and pressure. This method is described below in a little more detail.

Specifically, the method measures simultaneously pressure, strain, and temperature by combining frequency shifts in two scattered lights of Brillouin and Rayleigh scattering, and calculate these quantities using the following equations. That is, in the measurement method utilizing a Brillouin scattering frequency shift $\Delta v_B$ and a Rayleigh scattering frequency shift $\Delta v_R$ in a hybrid manner, the relationships between each frequency shift, and changes of strain, temperature and pressure are expressed as Eqs. (1) and (2) using sensitivity coefficients $C_{ij}$ (i=1 to 2, j=1 to 3) of the optical fiber.

$$\Delta v_B = C_{11}\Delta\varepsilon + C_{12}\Delta T + C_{13}\Delta\Delta P \tag{1}$$

$$\Delta v_R = C_{21}\Delta\varepsilon + C_{22}\Delta T + C_{23}\Delta\Delta P \tag{2}$$

Since the sensitivity to pressure change $\Delta P$ is generally smaller compared to the other two terms in the equations (see Patent Document 3), direct measurement of pressure is abandoned here. Instead, by neglecting blood pressure exerted on the optical fiber, the following Eqs. (3) and (4) simplified from Eqs. (1) and (2) are used for the calculation.

$$\Delta v_B = C_{11}\Delta\varepsilon + C_{12}\Delta T \tag{3}$$

$$\Delta v_R = C_{21}\Delta\varepsilon + C_{22}\Delta T \tag{4}$$

Furthermore, the present invention proposes a technology of precisely measuring a pressure distribution by providing a structural member (see the reference numeral 4 in FIG. 3) for continuously converting blood pressure to strain of the optical fiber. While the present invention proposes a technology of determining pressure by measuring stain with an inorganic glass based optical fiber, an organic optical fiber will enable direct pressure measurement using Eqs. (1) and (2). Giving initial values $\varepsilon_0$ and $T_0$ for the strain change $\Delta\varepsilon$ and the temperature change $\Delta T$, a strain $\varepsilon$ and a temperature T at a given position are calculated from the above calculated $\Delta\varepsilon$s, $\Delta T$s, since these values are measured as, for example, continuous values (distributed values) at longitudinal positions of the optical fiber.

In more detail, in the simultaneous measurement of multiple quantities using such the hybrid technique, measurement error may in some cases be reduced in such a way that a frequency shift $\Delta v_R$ of Rayleigh scattering and a frequency shift $\Delta v_B$ of Brillouin scattering are simultaneously measured and then the Brillouin scattering frequency shift $\Delta v_B$ is filtered using the Rayleigh scattering to further improve measurement accuracy. FIG. 1 shows examples of measured relationships between each frequency shift and pressure. In this measurement, using a hybrid measurement technique such as a tunable wavelength coherent optical time domain reflectometry (TW-COTDR) or a Brillouin optical correlation domain analysis (BOCDA) will allow for achieving accuracy of 0.079 με for strain and accuracy of 0.009° C. for temperature. In addition, the frequency measurement accuracy is ensured up to a frequency allowance of the laser (for example, 12 MHz), and the ensured frequency measurement accuracy corresponds to pressure accuracy of 19 kPa (=3 psi) in Eqs. (1) and (2) if not neglecting strain and temperature changes.

When an optical fiber covering member (protective film, specifically, formed of, for example, PFA: copolymer of tetrafluoroethylene and perfluoroalkyl vinyl ether) receives pressure, the effect of axially volumetric change affects axial strain of the optical fiber. Increasing the covering thickness will permit apparent pressure sensitivity to be enhanced when a covering member has stiffness lower than that of glass (see FIG. 2). However, the apparent pressure sensitivity is not so enhanced in actuality for the diameter of up to about 0.4 mm, which is a maximum requirement for vascular insertion, and is nearly equal to the data of 0.25 mm diameter.

Examining the fractional flow reserve (FFR) measurement concerned in the present invention, a pressure range to be measured is from −4.0 to 40.0 kPa (from −30 to 300 mmHg) and a temperature effect per degree Celsius is ±40.0 Pa/° C. Accuracy required for the measurement are about ±0.1 kPa (=±1%) for −4.0 to 6.7 kPa (−30 to 50 mmHg) and about ±0.3 kPa (=±3%) for −6.7 to 40.0 kPa (−50 to 300 mmHg) (see Non-Patent Document 2). In addition, a preferable external diameter of a usable catheter is supposed to be 0.46 mm or less (see Patent Document 2).

The above-described pressure measurement accuracy is not so expected by the effect of the optical fiber covering member, in comparison to the pressure accuracy in the technology of measuring simultaneously pressure, temperature, and strain by the hybrid measurement method, to which the present application intends to apply, using the combination of Brillouin and Rayleigh scattered light. Accordingly, an ordinary usage of optical fiber sensor probably cannot satisfy the pressure measurement accuracy.

The present invention is made to resolve the above-described problems, and is aimed at measuring separately two or more mixed physical quantities of an object to be measured as independent parameters by measuring simultaneously the two or more physical quantities such as temperature of the object to be measured and strain converted from pressure of the object using an optical fiber and by analyzing the measured data, and is aimed at implementing a multifunctional measurement with a small number (two or less) of optical fibers.

Means for Solving the Problem

A fiber optic in vivo diagnostic sensor system according to the present invention includes a blood vessel insertable pressure distribution measurement device to be inserted in vivo into a blood vessel to measure distributions of temperature and pressure of an object to be measured along a predetermined site. The measurement device has an outer layer deformable by external pressure and preventing the to-be-measured object from entering into the inside of the outer layer; a single mode optical fiber deformable by temperature and strain; and a structural member disposed so as to be in contact with the single mode optical fiber at a center axis portion or an outer circumferential portion of the structural member, to transfer pressure applied to the outer layer and to convert continuously the pressure to strain of the optical fiber. The sensor system further includes a measurement unit emitting laser light into the single mode optical fiber, detecting continuously a scattered light frequency shift produced in the single mode optical fiber and calculating a blood pressure at a given position of the single mode optical fiber from a temperature change and a strain change of the optical fiber that are calculated from the detected scattered light frequency shift; a memory unit storing the calculated value calculated in the measurement unit; and an analyzed/display unit performing desired analysis and display on the basis of the calculated value stored in the memory unit.

A blood vessel insertable pressure distribution measurement device according to the present invention is to be inserted in vivo in a blood vessel to measure distributions of temperature and pressure of an object to be measured along a predetermined site. The measurement device includes an outer layer deformable by external pressure and preventing the to-be-measured object from entering into the inside of the outer layer; a single mode optical fiber deformable by temperature and strain; and a structural member disposed so as to be in contact with the single mode optical fiber at a center axis portion or an outer circumferential portion of the structural member, and being fixed to a plurality of portions of the optical fiber or being in contact with a plurality of portions of the optical fiber, to transfer pressure applied to the outer layer and to convert continuously the pressure to strain of the optical fiber.

Advantages of the Invention

According to a fiber optic in vivo diagnostic sensor system of the present invention, a plurality of physical quantities of an object to be measured can be measured continuously and accurately as separated independent parameters. Moreover, even for a plurality of sites to be measured, the accurate measurement can be performed at one time. Further, the sensor system brings about an effect that versatile measurement can be implemented with two or less optical fibers. Furthermore, the measurement can be performed even for a smaller blood vessel than conventional measurements, and a safer measurement having less potentiality of injuring a living body can be performed when obtaining in vivo diagnostic data because there is no need to form apertures and the like in the outer circumferential layer of the measurement probe.

BRIEF DESCRIPTION OF THE DRAWINGS

FIGS. 7A and 7B are explanatory diagrams showing sensor portions fundamental to the fiber optic in vivo diagnostic sensor system according to Embodiment 1 of the present invention;

FIGS. 8A-8C are diagrams for explaining a model for evaluating the sensitivity of a structural member for the optical fiber according to Embodiment 1 of the present invention;

FIGS. 9A-9C 9A-9D are explanatory diagrams showing an example of the sensor portion of a structural member for the optical fiber in the fiber optic in vivo diagnostic sensor system according to Embodiment 1 of the present invention;

FIGS. 11A and 11B are explanatory diagrams of a sensor portion of the fiber optic in vivo diagnostic sensor system according to Embodiment 2 of the present invention;

FIG. 18 is a diagram showing an example of a sensor portion employed in a conventional in vivo diagnostic sensor system.

EMBODIMENTS FOR CARRYING OUT THE INVENTION

Figure 1:
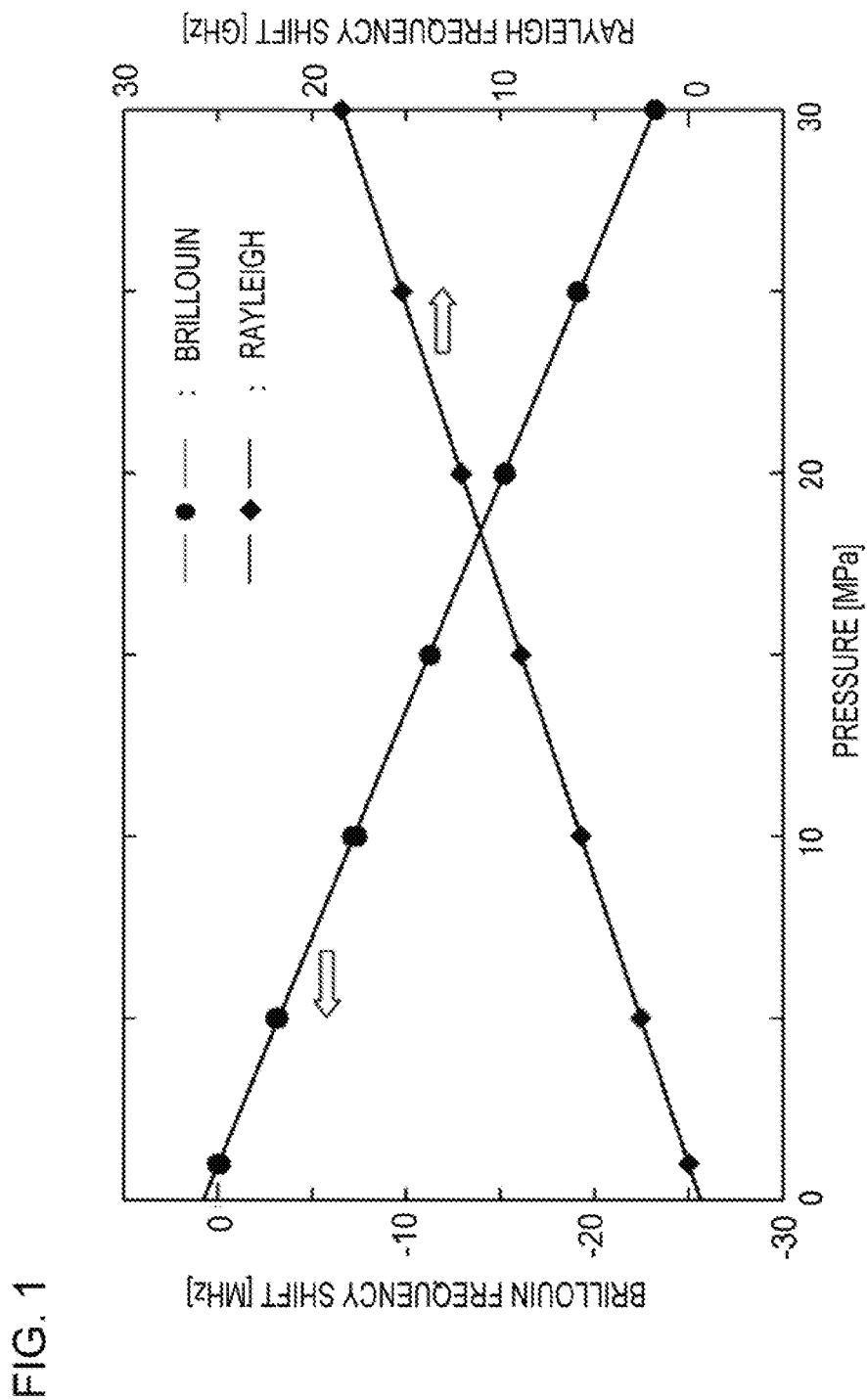
FIG. 1 is a graph showing examples of measured relationships between pressure and frequency shifts of Rayleigh scattering and of Brillouin scattering in an optical fiber.

Hereinafter, fiber optic in vivo diagnostic sensor systems of the present invention will be described with reference to the drawings. Note that components designated at the same reference numerals in the drawings express the same components, and the descriptions thereof are omitted.

Embodiment 1

Figure 3:
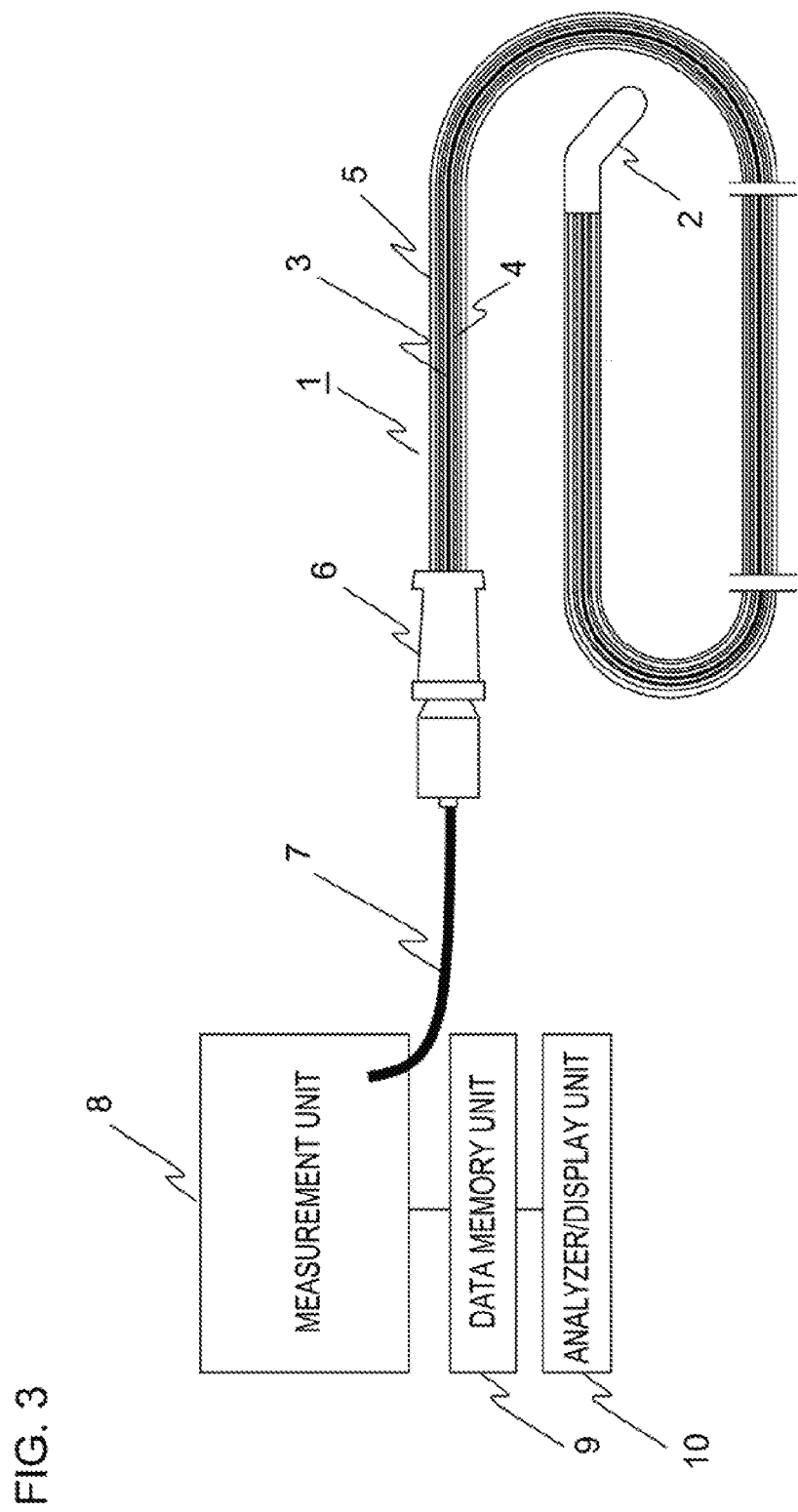
FIG. 3 is a diagram showing an example of a fiber optic in vivo diagnostic sensor system according to Embodiment 1 of the present invention.

A fiber optic in vivo diagnostic sensor system according to Embodiment 1 of the present invention is described first with reference to FIG. 3. The system described in Embodiment 1 is a base system of the fiber optic in vivo diagnostic sensor systems of the present invention. This sensor system stores sensor outputs, as fundamental data for in vivo diagnosis, obtained from a sensor-functional optical fiber provided to a blood vessel insertable pressure distribution measurement device 1 (hereinafter, referred to as "catheter" in the present invention) that is a constituent component of this system and inserted in vivo into a blood vessel under measurement, and then analyzes and displays the data. In the figure, the catheter 1 is equipped with a J-tip 2 at its head, which is a guide for affiliating insertion of the catheter into a blood vessel. The leading portion of the J-tip 2 is bent obliquely with respect to the catheter axis and the proximal end thereof is connected with a metal structural member 4 made such as of stainless steel. In some cases, a spiral wire may be attached circumferentially around a portion of the catheter, which portion is connected to the proximal end of the J-tip 2 and corresponds to the distal portion of the sensor (described later in detail). The catheter 1 has an outer layer 5 formed of rubber or a flexible skin material harmless to the human body. Blood under measurement does not enter into inside the outer layer 5, but the blood pressure transfers to the structural member 4 via the flexible outer layer 5. The structural member 4 has a function of converting the applied pressure to a longitudinal stretch, which causes a longitudinal stretch deformation of a sensor-functional single mode optical fiber 3 (abbreviated hereinafter as "SM fiber") disposed in the structural member. At the proximal portion of the catheter 1, an operating handle 6 is provided for maneuvering the principal movement of the catheter. Although the SM fiber 3 is in no direct contact with blood, since stretch of the structural member 4 is proportional to blood pressure, axial strain of the SM fiber 3 is proportional to the blood pressure under measurement, or can be converted therefrom. In addition, a jacket (not shown) for guiding in vivo insertion of the catheter 1 may in some situations be provided circumferentially around the catheter 1 at the insertion portion of the body surface. In actuality, since the temperature of a blood vessel along a site under measurement or of the whole blood vessels of a patient is normally non-uniform, the measurement method is demanded that takes into account the non-uniformity in temperature. Hence, the measurement method must be able to also measure the temperature when the pressure is measured. The sensor output detected by the SM fiber 3 is input to a measurement unit 8 through multiple SM fibers 7 connecting between the catheter 1 and the measurement unit. The measurement unit 8 measures (processed synchronously with a sync signal as may be necessary) the output as signals, such as a Brillouin scattering frequency shift $\Delta v_B$ and a Rayleigh scattering frequency shift $\Delta v_R$, to output to a data memory unit 9 the measured signals as data such as of a blood temperature distribution and a converted blood pressure distribution along the blood vessel. Then, an analyzer/display unit 10 analyzes the data accumulated in the data memory unit 9 to calculate desired diagnostic data such as a fractional flow reserve (FFR), and outputs as signal data the blood pressure distribution data of the site under diagnosis. These data is graphically displayed, as may be necessary, on a display or the like provided to the analyzer/display unit 10.

Figure 4:
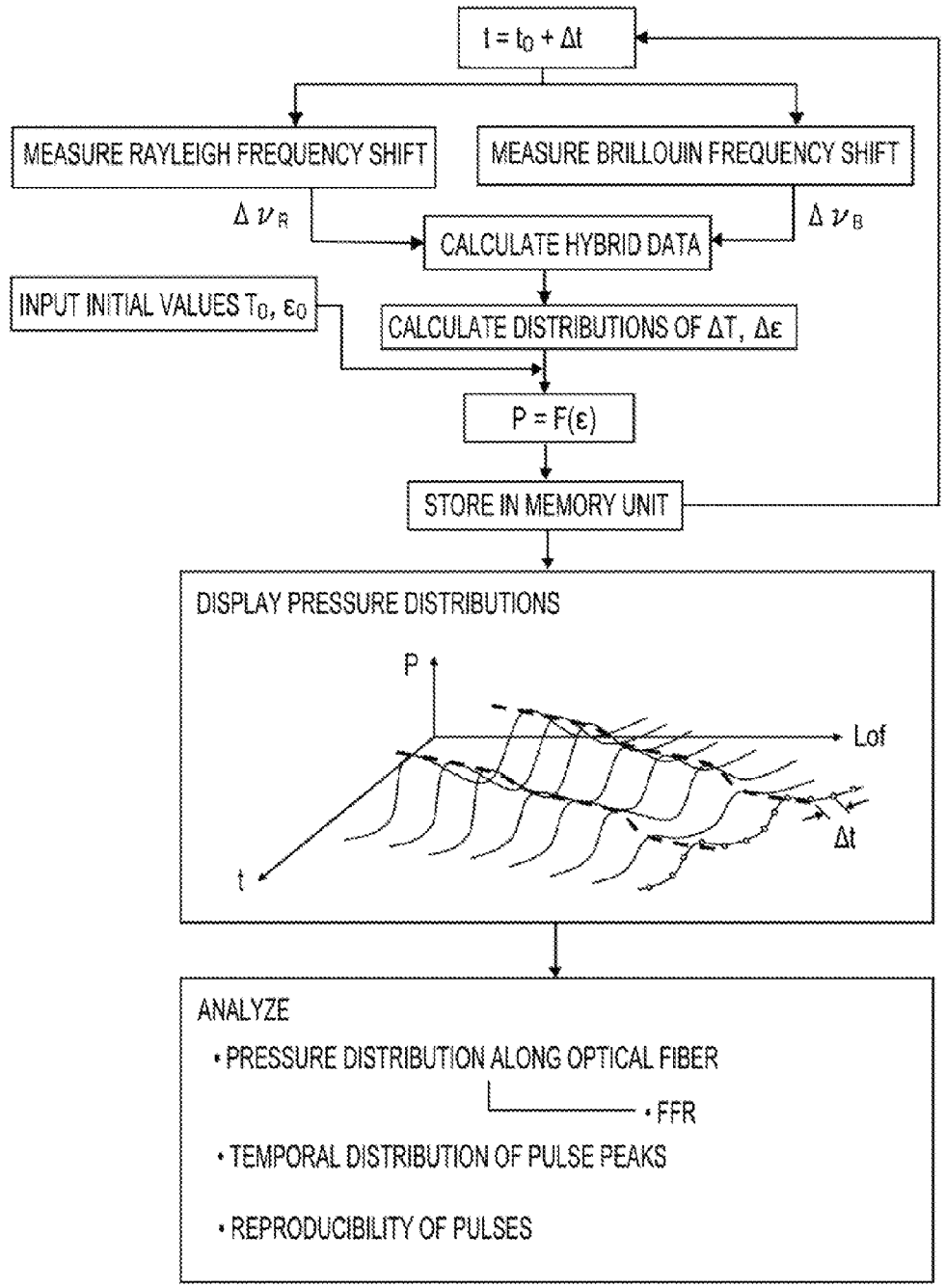
FIG. 4 is a flow diagram showing a procedure and an outline of measurement, analysis, and display performed by the fiber optic in vivo diagnostic sensor system according to Embodiment 1 of the present invention.
Figure 15:
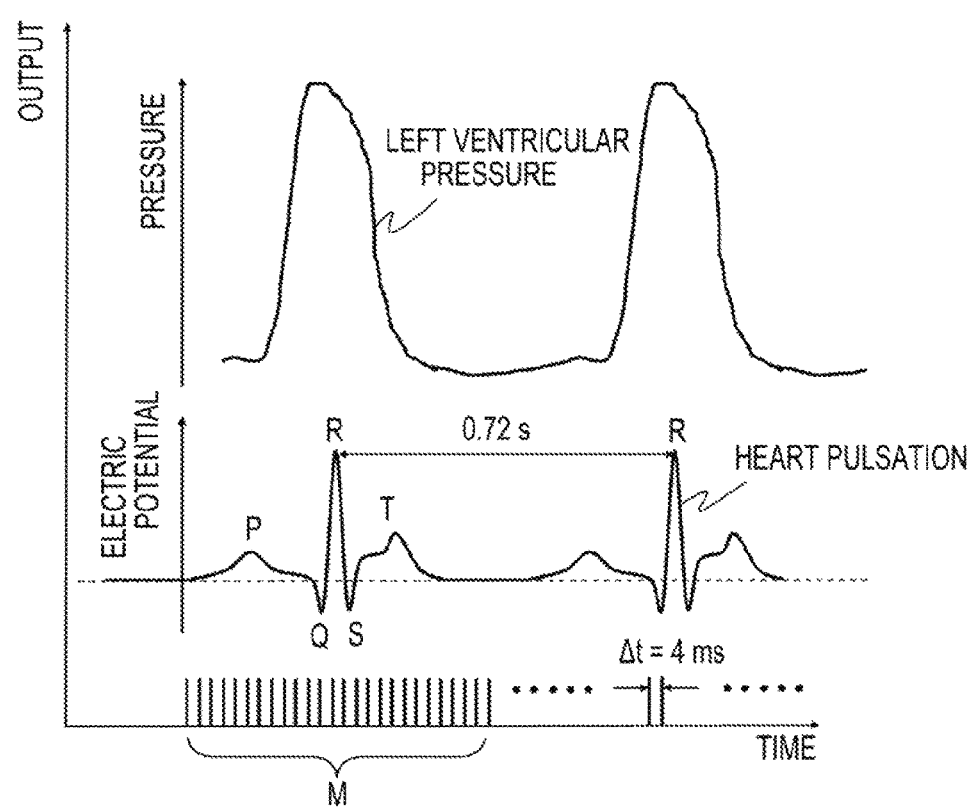
FIG. 15 is a model graph for explaining heart pulsation.

The above-described measurement procedure is summarized in FIG. 4. In the figure, a measurement start time (triggered by the measurement unit 8) is defined as $t_0$, and the measurement with the SM fiber 3 is repeated at time intervals $\Delta t$. A Rayleigh scattering frequency shift $\Delta v_R$ and a Brillouin scattering frequency shift $\Delta v_B$, which are sensor outputs, are measured during each measurement interval. Next, distributions of temperature change $\Delta T$ and strain change $\Delta \varepsilon$ are calculated for measurement positions using the two frequency shifts $\Delta v_R$, $\Delta v_B$ and reference state temperature $T_0$ and strain $\varepsilon_0$ input preliminarily as initial values to the measurement unit 8 (see Eqs. (3) and (4)). Next, the measurement unit 8 calculates a desired blood pressure (pressure) P as a conversion value using a function of strain $\varepsilon$. Then, the pressure P calculated by the measurement unit 8 is output to and stored in the data memory unit 9 in. The analyzer/display unit 10 later analyzes the data accumulated in the data memory unit 9 to display the data as a distribution of pressure P at a time t in a desired display format. In the above measurement, the time interval $\Delta t$ needs to be 1/100 seconds or shorter as a guideline to follow blood pulsation in a time-resolved manner so that distributions at each time interval can be obtained (FIG. 15 shows an example of a case of 1/250 seconds). And then, a fractional flow reserve (FFR) and the like are calculated using a distribution of maximum pulse pressures.

Figure 5:
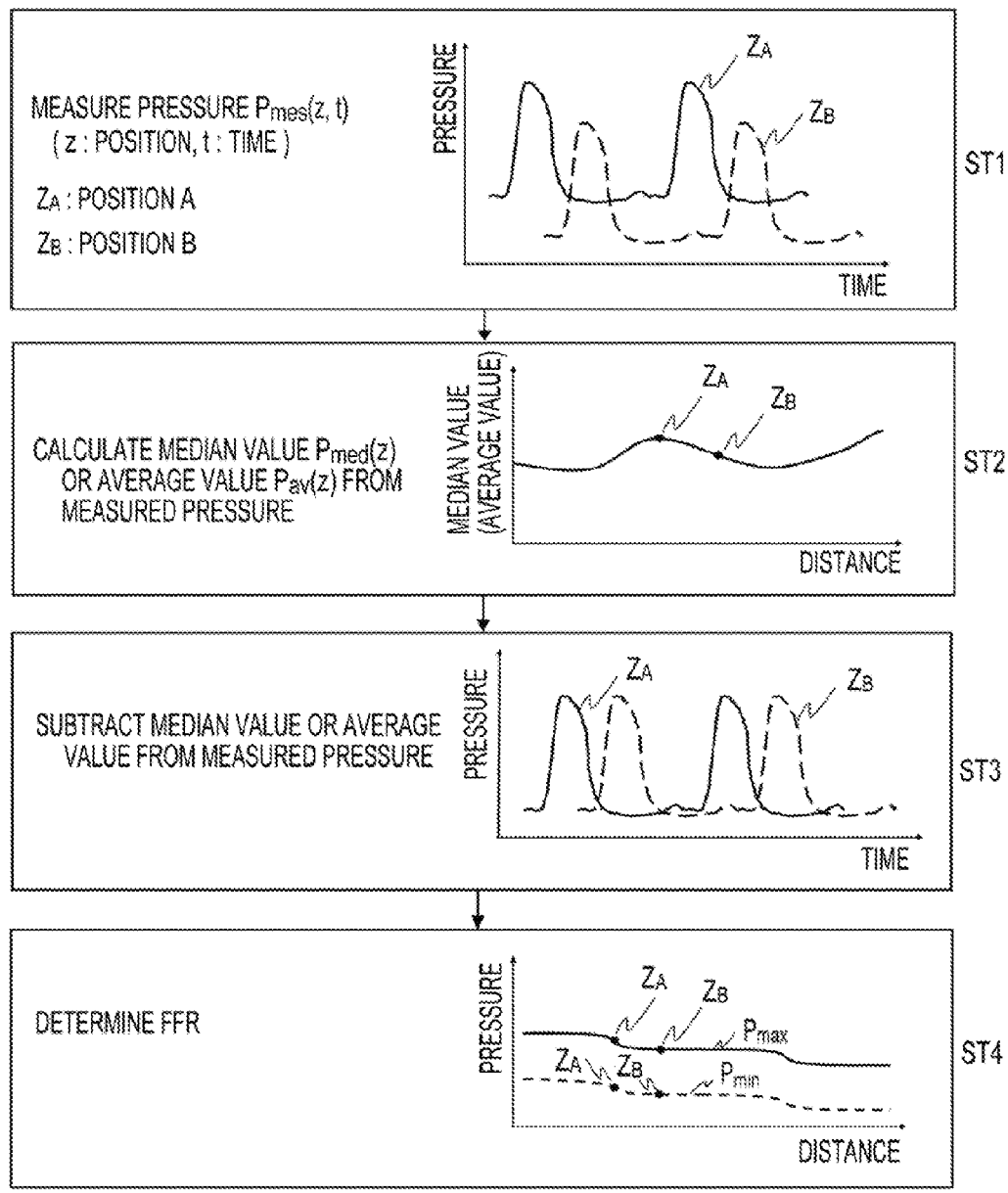
FIG. 5 is a flow diagram for determining the FFR.

A procedure of determining the fractional flow reserve (FFR) is explained in more detail with reference to FIG. 5. Since the pressure P is calculated as a function of a position ($L_{of}$) and time t as shown in FIG. 4, defining the coordinate of the position as z, a measured pressure P can be expressed as $P=P_{mes}(z, t)$. The measured pressure $P_{mes}(z, t)$ possibly includes influence of a static strain produced when the catheter 1 is inserted. Hence, a method of removing the static strain influence using measured pressure values calculated for two positions A and B is explained with reference to FIG. 5. In Step ST1 of FIG. 5, a pressure $P_{mes}(z, t)$ is measured. Note that in the graph shown in ST1, a pressure $P_{mes}(z, t)$ measured at a position A is designated at $Z_A$ and a pressure $P_{mes}(z, t)$ measured at a position B is designated at $Z_B$, and the vertical axis represents pressure and horizontal axis represents elapsed time after start of the measurement. The graph in ST1 shows a model diagram of measured waveforms illustrating left ventricular pressure change during two heartbeats. Next, in Step ST2, the median value of measured pressure $P_{mes}(z, t)$ at the position A or the position B is calculated from Eq. (5), or an average value thereof at the position A or the position B is calculated from Eq. (6) (the integral sign "∫" is used in Eq. (6)).

$$P_{med}(z) = \frac{P_{mes}^{max} + P_{mes}^{min}}{2} \quad (5)$$

$$P_{av}(z) = \frac{\int P_{mes} dt}{\int dt} \quad (6)$$

These values are calculated for all positions under measurement. Next, in Step ST3, the median value $P_{med}(z)$ or the average value $P_{av}(z)$ calculated in ST2 is subtracted from the measured value $P_{mes}(z, t)$, and the subtracted value of the pressure is expressed as P(z, t) (see Eq. (7) or (8), respectively).

$$P(z,t)=P_{mes}(z,t)-P_{med}(z) \quad (7)$$

$$P(z,t)=P_{mes}(z,t)-P_{av}(z) \quad (8)$$

By this subtraction, the static strain at the insertion of the catheter is cancelled out. Finally, in Step ST4, the value of a pressure P(z, t) is calculated for each position by varying the measurement position and then the pressure change is plotted taking z as a horizontal axis (distance). The FFR determination is performed by calculating an FFR from the pressure change.

Figure 6A:
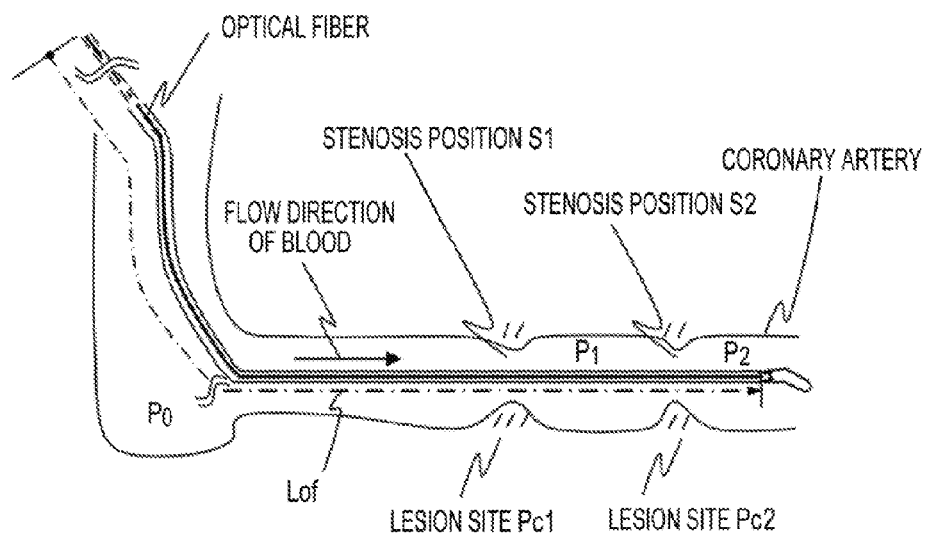
FIGS. 6A and 6B are model diagrams showing stenotic lesion sites of a blood vessel and pressure changes at the stenotic lesions sites.
Figure 6B:
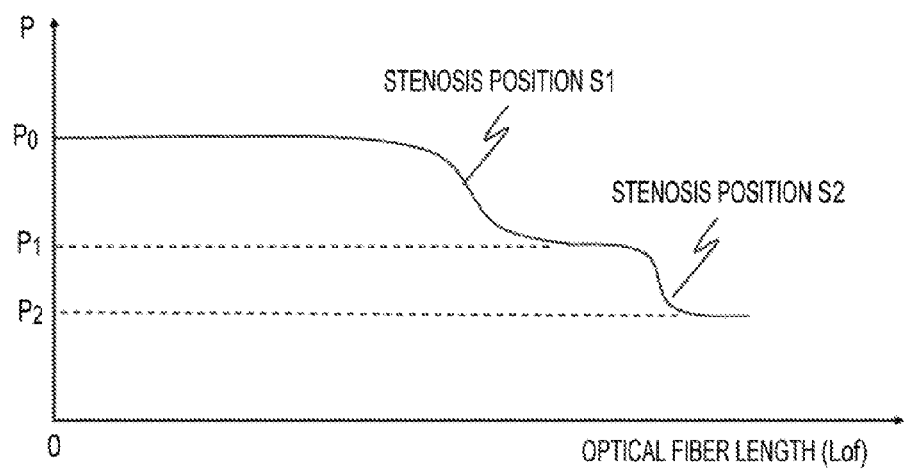

As described above, according to Embodiment 1, blood pressure in a blood vessel to be measured can be measured in vivo continuously not only temporally but also spatially along a predetermined site using frequency shift data of the two kind scattered lights, thus bringing about an effect that a plurality of physical quantities under measurement can be measured in a single measurement by using the single SM fiber 3 only. Although a conventional point measurement sensor is difficult to measure a blood vessel having a plurality of vascular stenosis sites for the reason of its measurement probe structure, the present invention enables measurement even for such a plurality of vascular stenotic sites because of the continuous measurement capability (see FIGS. 6A and 6B). The fractional flow reserve (FFR) is expressed by $P_1/P_0$ or $P_2/P_0$ (here, $P_0$, $P_1$, and $P_2$ shown in FIGS. 6A and 6B are values obtained in accordance with the procedure described in ST1 through ST4). While FIGS. 6A and 6B show a situation of a plurality of vascular stenosis sites, the measurement is possible not only for that situation but also for a situation of a single vascular stenosis site, as a matter of course. For any situation of a single or a plurality of vascular stenosis sites, a stenosis site can be determined from the pressure measurement. It is therefore conceivable that measurement data obtained in this way is useful as in vivo diagnostic data.

The sensor portion used in the measurement is described in more detail. FIGS. 7A and 7B show cross sectional structures of typical sensor portions for the measurement. Referring to the figures, the J-tip 2 formed of plastic (for example, such as polyvinyl chloride) and having a obliquely bent portion is attached to the head of the catheter, and the SM fiber 3 is disposed on the center axis of the sensor portion connected to the J-tip. A structural member 4 for transferring external pressure and converting it to strain of the SM fiber 3 is disposed immediately around the SM fiber, and an outer layer 5 made such as of rubber is further disposed around the structural member (FIG. 7A). For ease of in vivo insertion of the catheter, a spiral wire layer 16 may in some cases be attached circumferentially around the outer layer (FIG. 7B). Even though the wire layer 16 is attached, since blood passes through the pitch spaces of the wire, the condition of the pressure applied to the outer layer 5 remains unchanged. The SM fiber 3 shown in the figures has an outer diameter of about 80 to 250 µm, and the structural member 4, which is disposed around the fiber and converts the applied pressure to stain, is a stainless steel formed protective layer for the SM fiber and has a function of proportionally converting ambient pressure to stretch in the longitudinal direction, i.e., the axial direction of SM fiber 3 (which is described below in a little more detail). This function allows for creating strain in the SM fiber proportionally to the pressure. Moreover, the catheter can be formed to have an external diameter of 0.4 mm. Therefore, the sensor satisfies specifications for an in vivo diagnostic sensor to which the present invention intends to apply, so that it can be successfully used in pressure or velocity measurement for PCI. Furthermore, pressure (blood pressure) can be measured in vivo even though the diameter of a blood vessel to be measured is relatively small.

Figure 2:
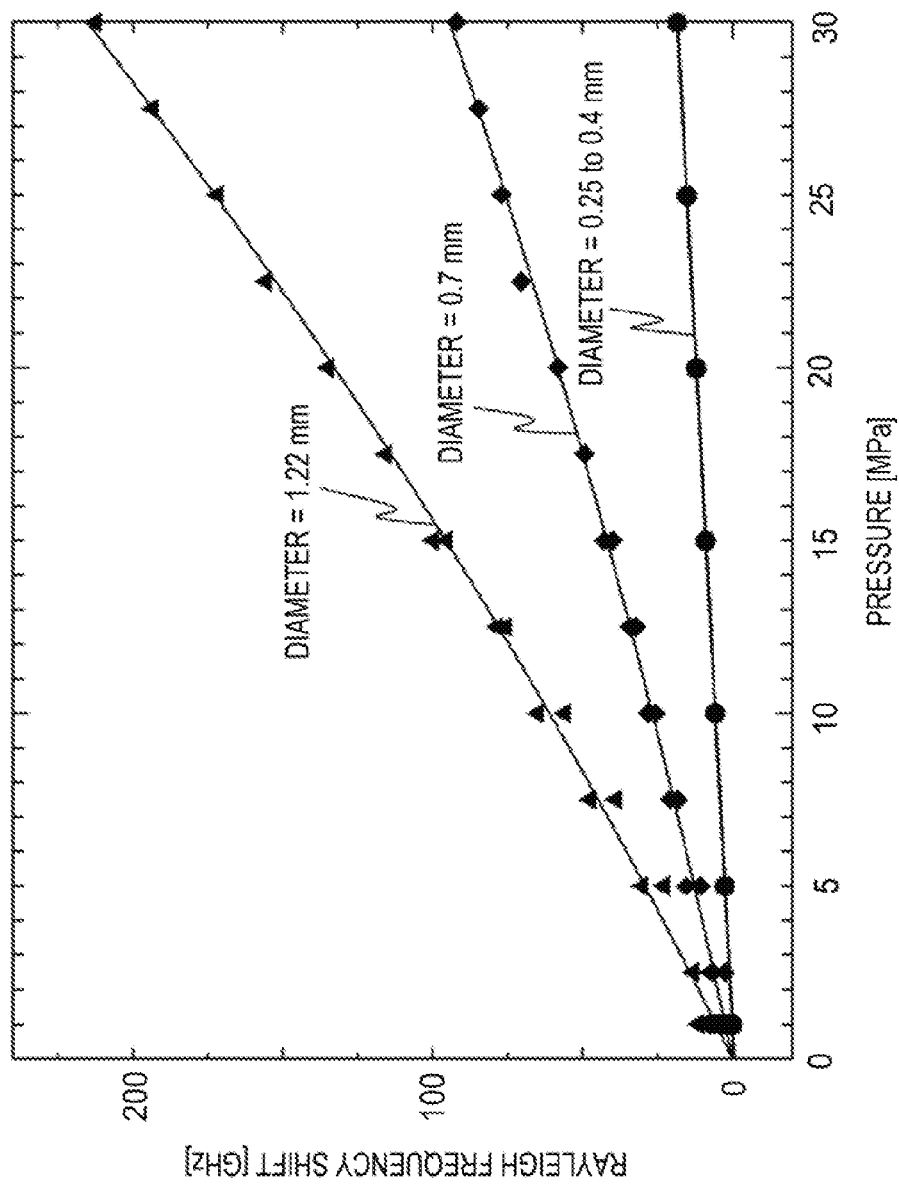
FIG. 2 is a graph showing examples of measured relationships between pressure and Rayleigh scattering frequency shifts when varying optical fiber diameter.

It is also conceivable that the structural member 4 is integrally formed as a member for covering the SM fiber. Since the integral structure of the covering member alters the pressure transferring, the sensitivity of the SM fiber may possibly enhance. When the stiffness of the covering member is lower than that of glass, increasing the thickness of the member will allow for enhancing apparent pressure sensitivity, as described above (see FIG. 2). However, in the pressure or velocity measurement for PCI to which the present invention intends to apply, since the catheter needs to have an external diameter of about 0.4 mm or less as has been described above, it is not expected to enhance the pressure sensitivity more than several times by increasing the thickness. Forming the SM fiber itself of plastic having low stiffness is also effective for the enhancement. For that reason, described below is a structural member that has a continuous, precise, uniform and simple structure and is suitable for converting distributed pressure into continuous strain.

First, in order to evaluate the sensitivity of a structural member suitable for such a pressure-strain conversion is examined using a structural model shown in FIGS. 8A and 8B. The element of the model in FIG. 8A is such that apertures having a diameter D are formed in the outer circumferential surface of a cylindrical measurement probe having the SM fiber disposed on the center axis and an external pressure is exerted on the apertures. Here, the model simulates the measurement probe, and the external pressure at the apertures corresponds to blood pressure. Since the probe generally has an axisymmetric structure, FIG. 8B shows only half portion thereof. Two elastic bars having the same shape and arranged obliquely (at an angle θ) with respect to the SM fiber are supposed to receive an external pressure (pressure P) exerted on the aperture in the outer circumferential surface of the measurement probe. Specifically, it is supposed that the element has a height h, which is the distance from the outer circumferential surface of the measurement probe to the SM fiber, and the elements are connected along the axis of the SM fiber at pitches L, the distance between A and B. In this model, it is considered that vertically exerting pressure P (corresponding to blood pressure exerting on the apertures) is separately supported by the same two bars disposed in a direction oblique by an angle θ with respect to the horizontal direction (the axial direction of the SM fiber) so as to produce equivalent axial component force Tc in the horizontal direction, as shown in FIG. 8C. The axial force Tc causes a stretching strain in the SM fiber, and the strain is the subject to be measurement.

The model is evaluated by substituting specific values. Since area of the aperture is $\pi D^2/4$, designating a blood pressure on the aperture at $P_b$, an external force (pressure P) is expressed as $P=P_b \times (\pi D^2/4)$. Letting $P_b=100$ N/m$^2$ and D=0.25 mm, the force is calculated as $P=100$ N/m$^2 \times 4.9 \times 10^{-8}$ m$^2 = 4.9 \times 10^{-6}$ N. And letting L=10 mm and h=0.2 mm, the value of the tangent function is tan θ=0.2/5=0.04. Hence, θ≈tan θ≈sin θ is holds true when the angle θ is regarded as θ<<1. Accordingly, the axial component force is calculated as $T_c=P/(2 \times \sin \theta)=4.9 \times 10^{-6}$ N/(2×0.04)≈$6.13 \times 10^{-5}$ N. While a strain of 1020 με is produced in a typical optical fiber against an axial force of 1 N, the strain ε in this case is $6.25 \times 10^{-2}$ με. Since it is empirically considered that a strain level of about 1 με is required, a probe structure (catheter structure) to be employed needs to satisfy the strain level.

For example, a stainless steel frame structure shown in FIGS. 9A-9C is proposed as a suitable structural member for the optical fiber. The figures show a structural member 4 that actually produces the above strain level in an optical fiber (the SM fiber here) by converting pressure to strain. A stainless steel frame 11 is fixed with glue to the SM fiber 3 at both positions (fixing positions) separated by a pitch L (see the position C1-C1 in FIG. 9A and the cross section C1-C1 in FIG. 9B). The stainless steel frame 11 has a structure bulging outwardly by a size of h from the SM fiber axis. In addition, the upper and lower envelope lines in FIG. 9A show the maximum diameter of the bulge portions of the stainless steel frame 11 and also show the contact line between the bulge potions and the outer layer 5 transferring external pressure to the sensor, as shown in FIG. 9C. As shown in the left figure of FIG. 9B, at the fixing portions (indicated by the cross section C1-C1), the stainless steel frame 11 is concentrically fixed around the SM fiber 3 with glue 12. Except for the fixing portions, the SM fiber 3 and the stainless steel frame 11 are coaxially from each other, and the stainless steel frame 11 is arranged in a circular-arcs separated by 120 degrees from each other in cross sectional planes so that a hollow space is formed between the outer layer and the SM fiber, as shown by the cross section D1-D1 as a typical example in the right figure of FIG. 9B. In addition, when the structural member for the optical fiber is actually used, since the outer circumferential portions of the stainless steel frame 11 are covered with the annular outer layer 5 as shown in FIG. 9C, the blood pressure is transferred as external pressure to the stainless steel frame 11 via the outer layer 5.

In this way, the blood pressure is transferred as external pressure via the outer layer 5 and the stainless steel frame 11 (which may also be called the structural member 4) to the SM fiber, to which the stainless steel frame 11 is fixed, through the contact portions (portions shown by the cross section D1-D1 of the stainless steel frame 11 in FIG. 9B), thereby to produce an axial strain in the SM fibber. This causes a frequency shit of the scattered laser light in the SM fiber, thus enabling the precise blood pressure measurement. In addition, the structural member 4 maintains the stiffness of the catheter as a whole and connects the J-tip to the steering handle 6 so that the J-tip can be torqued by maneuvering the steering handle 6. Further, it is also possible to measure the scattered light using a double end technique by providing a reflector device such as an FBG at the distal end of the measurement portion of the SM fiber. With such a technique, resolution in measurement of the Brillouin scattering frequency shift $\Delta v_B$ can be improved, thus enhancing accuracy of the calculated values based on the measurement data.

Embodiment 2

In Embodiment 1, desired data is obtained by measuring frequency shifts in two kinds of back scattered laser light with single SM fiber 3, as described above. In Embodiment 2, a fiber optic in vivo diagnostic sensor system that obtains desired data using only one kind of scattered light is described with reference to FIGS. 10 to 13.

Figure 10:
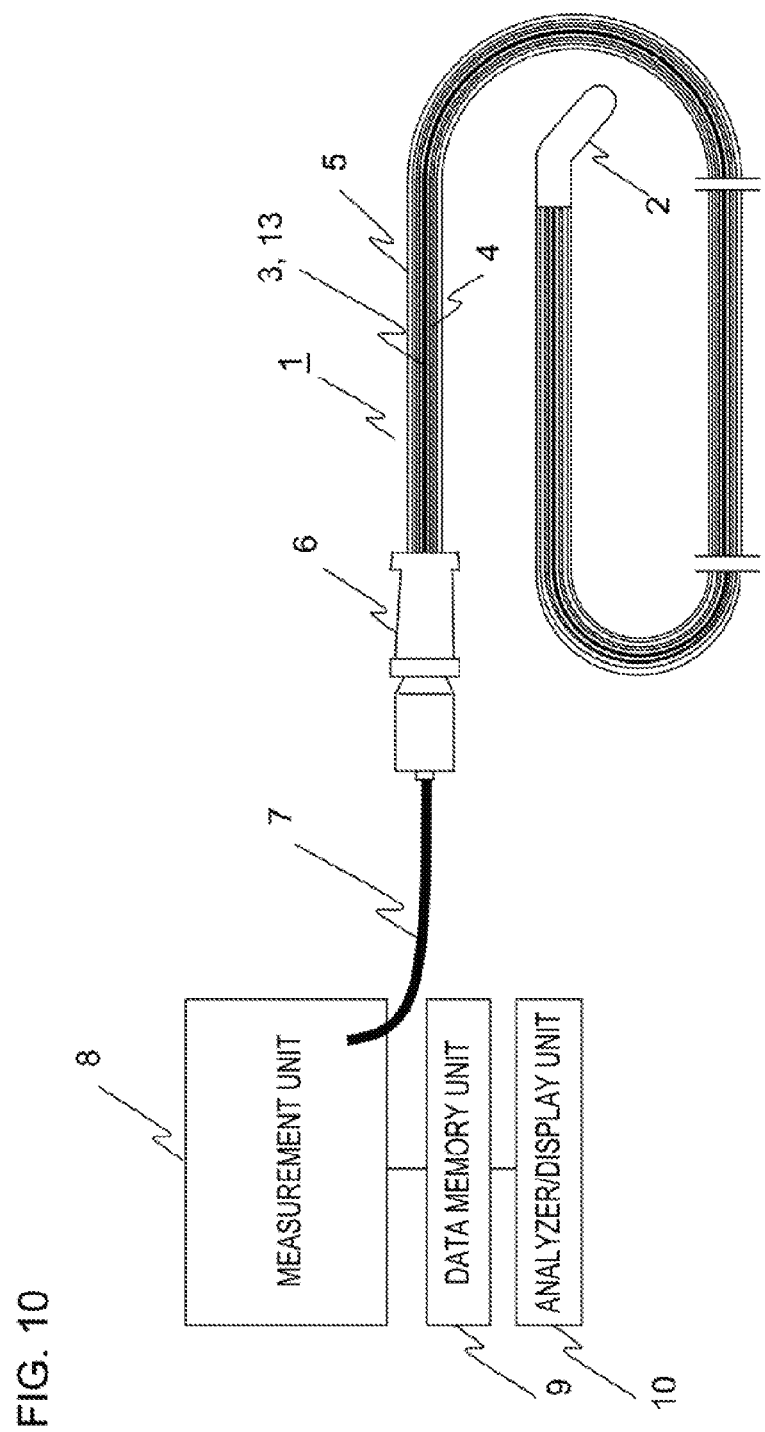
FIG. 10 is a diagram showing an example of a fiber optic in vivo diagnostic sensor system according to Embodiment 2 of the present invention.

First, an example of a system configuration according to Embodiment 2 of the invention is shown in FIG. 10. In the figure, another SM fiber 13 is disposed as a sensor fiber aside from the SM fiber 3 shown in Embodiment 1. In this configuration, the SM fiber 3 is subjected to the transferred pressure and is used as a pressure measurement fiber, while the SM fiber 13 is ordinarily disposed so as not to be subjected to the transferred pressure and is used as a temperature measurement fiber. In Embodiment 2, utilizing the fact that the sensitivity coefficients for the Rayleigh scattering frequency shift are larger than those for the Brillouin scattering frequency shift, not the Brillouin scattering frequency shift $\Delta v_B$ but the Rayleigh scattering frequency shift $\Delta v_R$ only, among frequency shifts produced in the scattered laser light, is used for the measurement with the SM fibers 3 and 13. In that case, Rayleigh scattering frequency shifts $\Delta v_R$ may be measured simultaneously with the SM optical fibers 3 and 13. Since the other constituent components are the same as with Embodiment 1, the explanation about them is omitted here.

FIGS. 11A and 11B are detailed diagrams showing a structure of the sensor portion, a probe for measuring blood pressure, of the catheter equipped with the two SM fibers. Referring to the figures, a stainless frame 11, which is a structural member, having an external shape like a rugby ball and a hollow space, is arranged around the SM fiber 3 (used for measuring blood pressure or the like) disposed along the center axis. An outer layer 5 for transferring external blood pressure and for protecting the SM fiber and the structural member is further disposed around the frame so as to be in contact with the stainless steel frame 11 at the maximum diameter portions thereof (see FIGS. 11A and 11B). The SM fiber 13 is disposed, aside from the SM fiber 3, near the outer layer of the catheter and in the hollow space of the structural member 4 so as not to be in contact with the structural member 4 and the outer layer 5, as shown in FIG. 11B. The SM fiber 13, since it is free without being fixed in the axial direction of the SM fiber and subjected to no external blood pressure, can measure a Rayleigh scattering frequency shift $\Delta v_R$ caused by a temperature change only.

Figure 12:
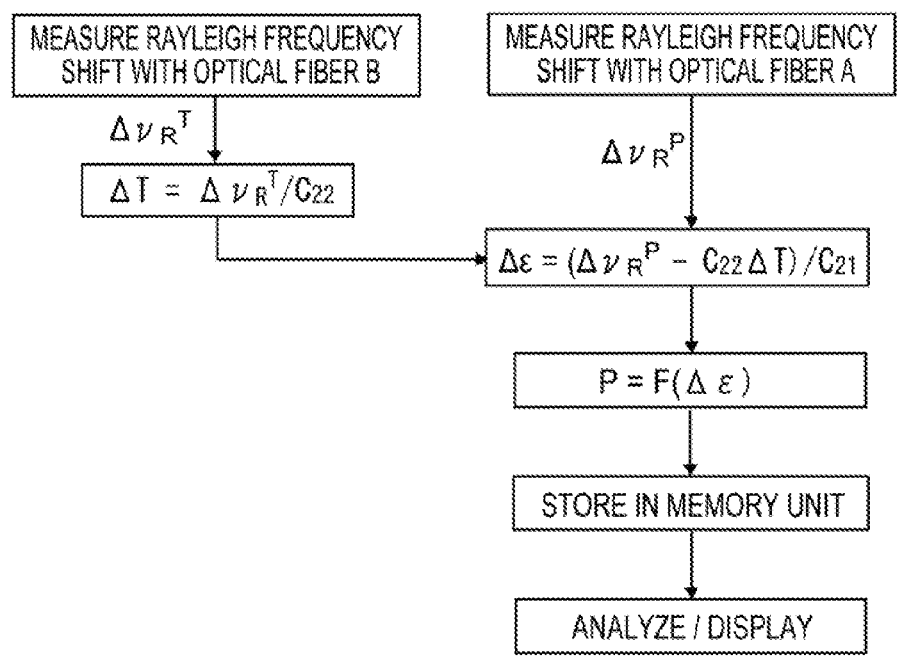
FIG. 12 is a flow diagram showing a procedure of measurement, analysis, and display performed by the fiber optic in vivo diagnostic sensor system according to Embodiment 2 of the present invention.
Figure 13:
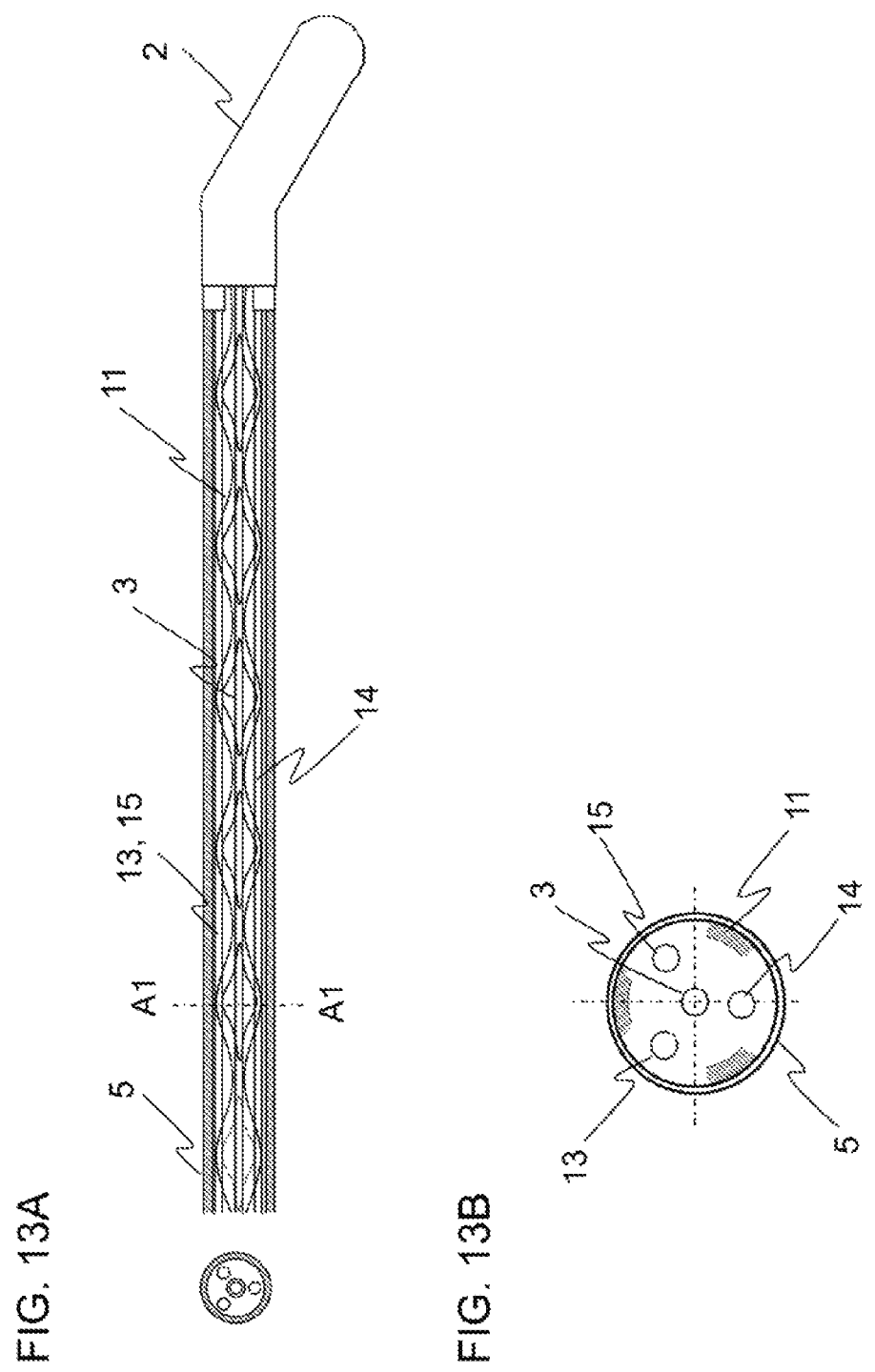
FIGS. 13A and 13B are explanatory diagrams of another sensor portion of the fiber optic in vivo diagnostic sensor system according to Embodiment 2 of the present invention.

Next, the outline of the analysis by the in vivo diagnostic sensor system according to Embodiment 2 is described with reference to the flow diagram of FIG. 12. An optical fiber B detects a Rayleigh scattering frequency shift $\Delta v_R$ that is caused only by a temperature change $\Delta T$. Designating the frequency shift at $\Delta v_R^T$, a temperature change is expressed as $\Delta T = \Delta v_R^T / C_{22}$ using the sensitivity coefficient $C_{22}$ for a temperature change of the optical fiber. Designating a Rayleigh scattering frequency shift measured with an optical fiber A at $\Delta v_R^P$, on the other hand, since no pressure exerts on $\Delta v_R^P$, the equation: $\Delta v_R^P = C_{21}\Delta\varepsilon + C_{22}\Delta T$ is holds true from Eq. (4) taking into account factors influenced by a strain change and a temperature change. Hence, a strain change is expressed as $\Delta\varepsilon = (\Delta v_R^P - C_{22}\Delta T / C_{21}$. Since temperature change values measured with the optical fiber A and the optical fiber B should be the same for an object under measurement, substitution of $\Delta T$ measured with the optical fiber B into the equation for calculating $\Delta\varepsilon$ of the optical fiber A leads to $\Delta\varepsilon = (\Delta v_R^P - \Delta v_R^T)/C_{21}$ (where the optical fibers A and B are supposed to have the same sensitivity coefficients $C_{22}$). Since $\Delta v_R^P$ and $\Delta v_R^T$ are known quantities measured with the optical fibers A and B, a strain $\Delta\varepsilon$ is calculated from these quantities using the above equation. Thus, pressure P can be calculated using a function of $\Delta\varepsilon$ ($P=F(\Delta\varepsilon)$). Note that the optical fiber A and the optical fiber B correspond to the SM fiber 3 and the SM fiber 13, respectively, when expressed by the numeral references used in FIGS. 10 and 11.

As described above, even in a measurement only using a Rayleigh scattering frequency shift $\Delta v_R$, employing the two-SM-fiber configuration in which one SM fiber subjected to no influence of pressure (blood pressure) is used as a means of measuring a frequency shift caused by a temperature change, Embodiment 2 can also bring about the same effect as Embodiment 1. In addition, in the case of using the structural member having the above structure to convert continuously pressure to strain with high sensitivity, it is conceivable in the present invention that further use of multiple FBGs can realize a simple sensor configuration. However, the resolution is restricted by the grating periods of the FBGs, and the length under measurement is also restricted.

While the configuration using two SM fibers as sensors is described above in Embodiment 2, a plurality of other optical fiber sensors can be further disposed in a catheter even considering into account the structural member 4 disposed around the fibers because the diameters of the two SM fibers are about 80 to 250 μm. Even when a plurality of other optical fibers are further disposed, the catheter can be formed to have a diameter of about 0.4 mm or less. An example of such a configuration is shown in FIGS. 13A and 13B. The figures show an example of disposing two optical fibers, for example, an endoscopic image fiber 14 and a tomographic image measurement fiber 15 (for example, for optical coherence tomography (OCT)) other than the two optical fibers 3 and 13. In addition, a tube for injecting a contrast agent may be disposed instead of the image fiber 14 or the OCT measurement fiber 15. Since a plurality (three or more) of optical fibers can be disposed in this way, a multi-functional measurement can be performed.

Embodiment 3

In actual measurements such as for PCI, an effect of heartbeat to blood pressure measurement may, in some cases, needs to be taken into consideration in addition to the above description. For dealing with such a situation, a measurement system according to Embodiment 3 is used. Specific examples are described below with reference to the figures.

Figure 14:
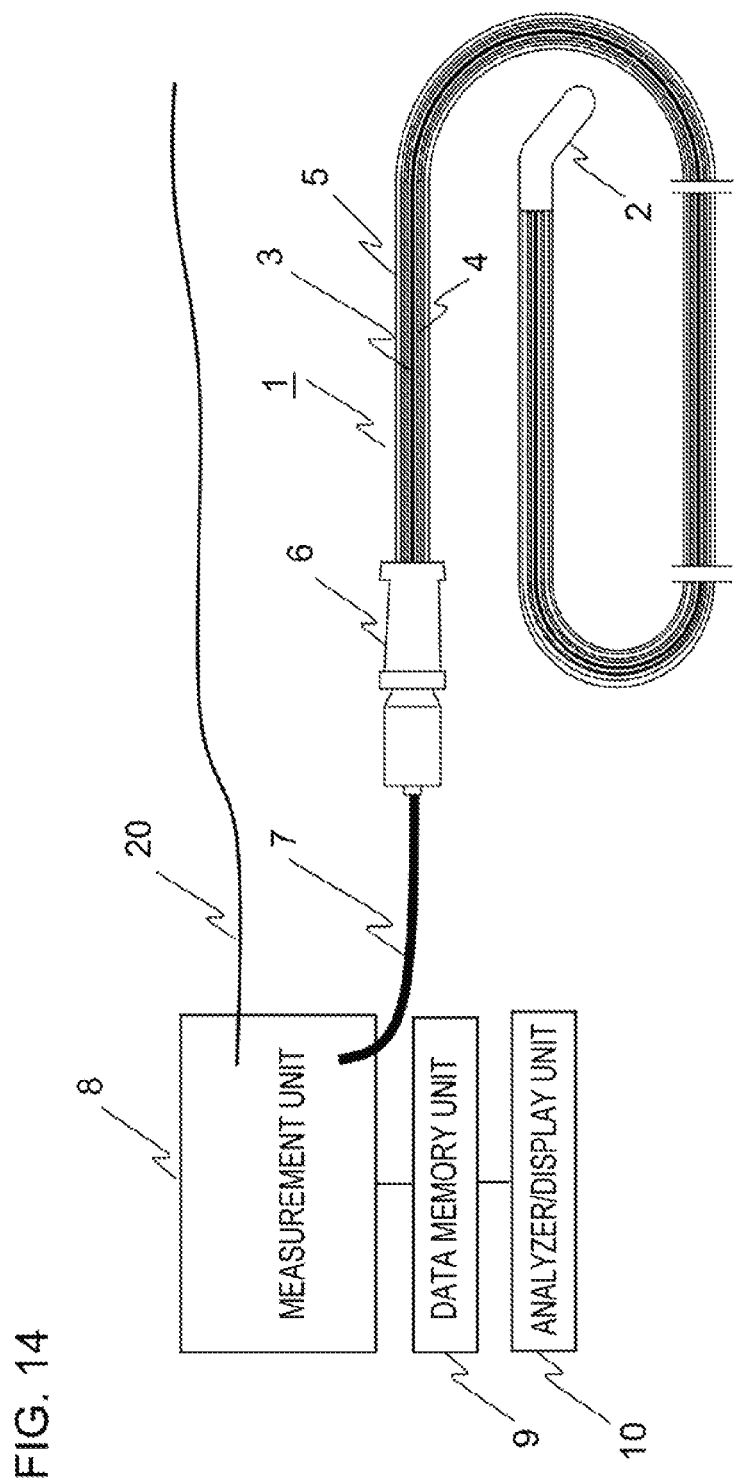
FIG. 14 is a diagram showing an example of a fiber optic in vivo diagnostic sensor system according to Embodiment 3 of the present invention.

FIG. 14 shows an example of a configuration of the measurement system according to Embodiment 3. As shown in the figure, a pulse detection fiber 20 is connected to the measurement unit 8 in addition to the SM fiber 3 shown in Embodiment 1. A heartbeat signal (the waveform shown in the middle of FIG. 15) detected by the pulse detection fiber 20 is measured with the measurement unit 8 in synchronism with a sync signal designated at M in FIG. 15, and then stored in the data memory unit 9. The waveform at the top in FIG. 15 is a model diagram showing an example of a left ventricular pressure change measured in synchronism with the sync signal, which shows that the pressure changes synchronously with electric potential of the heartbeat signal. In the system shown in FIG. 14, data such as pressure (blood pressure) detected by the SM fiber 3 is measured also with the measurement unit 8 in synchronism with the sync signal M, as with the heartbeat signal, and then stores in the data memory unit 9. Thus, both data, such as of heartbeat signal and pressure (blood pressure), measured in synchronism with the sync signal M can be compared on the same time base, so that analysis of the data allows for obtaining data such as of pressure (blood pressure) taken into account the influence of heartbeat to blood pressure measurement. Specifically, by measuring multiple times the pressure (blood pressure) with the fiber and the pulse with the pulse detection fiber 20 wound around a portion of an arm and then by averaging these measured data in synchronism with the sync signal, blood pressure data having an improved signal-to-noise ratio can be obtained, thus bringing about an effect such as of enhancing the accuracy.

While the SM fiber 13 connected to the measurement unit, which is described in Embodiment 2, is not shown in FIG. 14, in a measurement system configured such that the pulse detection fiber 20 is further connected to the measurement unit 8 in addition to the SM fiber 3 and the SM fiber 13 employed in the measurement system configuration of Embodiment 2, data such as of pressure (blood pressure) measured taking into account the influence of heartbeat to the blood pressure measurement can also be obtained, as described above in Embodiment 3.

That is, the fiber optic in vivo diagnostic sensor system according to Embodiment 3 allows for obtaining, as a result of analysis based on data measured with the pulse detection fiber 20, data such as of a temporal distribution of pulse peaks at a given position and reproducibility of pulses, with an accuracy of the sync signal interval (for example, about 4 msec (see FIG. 15) when using the system shown in FIG. 14).

Furthermore, data of change in the Young's elastic modulus of a blood vessel, data of irregular pulses and the like can be obtained, as basic in vivo diagnostic data, on the basis of data such as of temporal variation in pulse peaks and reproducibility of pulses. For example, since the Young's elastic modulus E, which indicates vascular stiffness, can be calculated from Moens-Korteweg equation: the following Eq. (9) (Non-Patent Document 3) if a pulse propagation velocity (also referred to as pulse wave velocity) v is obtained, it is considered that elastic modulus data during a certain time period is useful as diagnostic data for hardening of arterial blood vessels, $$E = 2\rho r v^2 / t_h \qquad (9)$$

where ρ is blood density; r, a blood vessel radius; and $t_h$, blood vessel thickness. In this way, temporal change data indicating hardening of arterial blood vessels can be obtained by comparing a pair of temporal change data sets measured during two different time periods, as shown by a displayed example in the flow diagram of Embodiment 1. Thus, it is expected that the temporal change data is more useful than before.

In the above description, while the structure of a structural member suitable for the optical fiber is described using the structural member shown in FIGS. 9A-9C (referred to as "Example 1"), a suitable structure is not limited to Example 1 but may be a structure described in the following Example 2 or Example 3. It should be noted that each embodiment of the present invention may be freely combined, or appropriately modified or omitted within the spirit and scope of the invention.

Example 2

Figure 16:
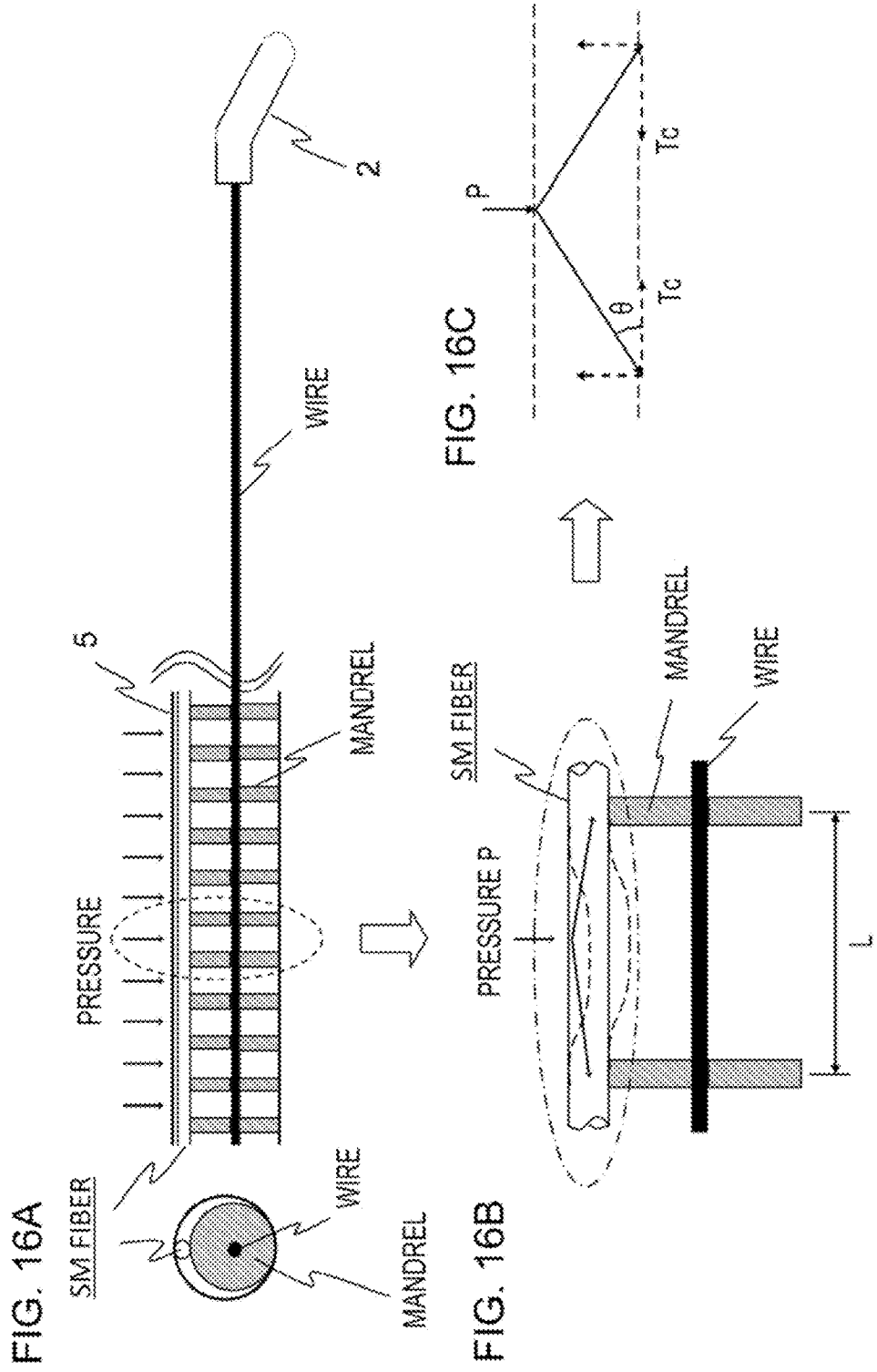
FIGS. 16A-16C are explanatory diagrams of a structural member for the optical fiber other than that employed in the fiber optic in vivo diagnostic sensor systems according to Embodiments 1 to 3 of the present invention.

FIGS. 16A-16C show another example of a suitable structure of a structural member for the single mode optical fiber. The single mode optical fiber is disposed away from the center axis of the measurement probe and inside near the outer layer 5, i.e., in the immediate vicinity thereof, and is fixed to mandrels joined to a wire (FIG. 16A). The pressure (blood pressure) applies to the outer layer 5 and puts it into contact with the optical fiber, i.e., the applied pressure P is transferred to the single mode optical fiber via the outer layer 5. As a result, the single mode optical fiber is fastened to the mandrels and deflected in the middle between the neighboring mandrels (see the broken line in FIG. 16B). In this structure, the mandrels are equivalent to the structural member 4 for converting pressure to strain. A modeling of a directional relationship between components of the pressure force is shown in FIG. 16C. An axial force designated at Tc is generated in the single mode optical fiber. In other words, FIGS. 16A-16C illustrate that one embodiment of the structural member is formed of a plurality of disk-shaped mandrels joined to an axial wire, and the single optical fiber is attached to a peripheral edge of each mandrel so as to be deflected radially inward between neighboring mandrels by pressure transferred via the outer layer.

Example 3

Figure 17:
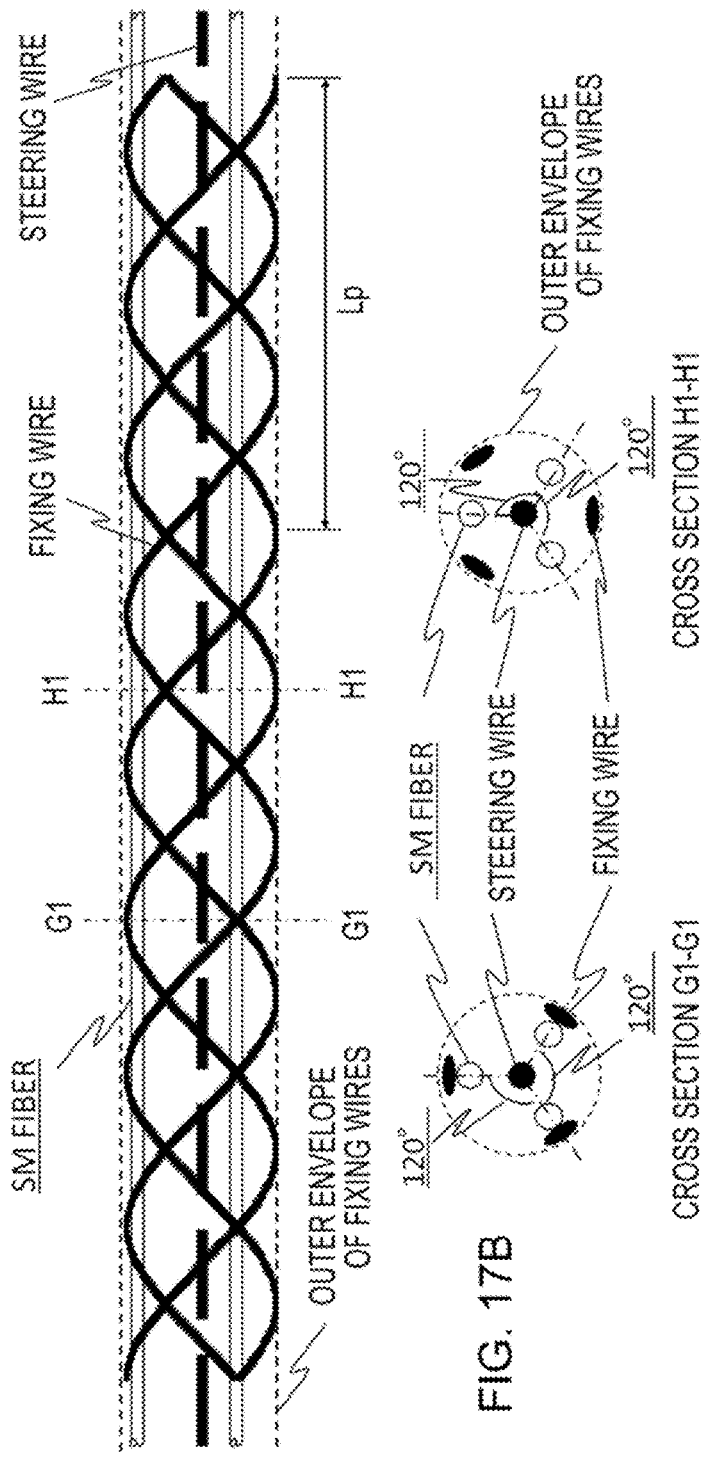
FIGS. 17A and 17B are diagrams for explaining another structural member for the optical fibers other than that employed in the fiber optic in vivo diagnostic sensor systems according to Embodiments 1 to 3 of the present invention.

FIGS. 17A and 17B show still another example of a suitable structure of a structural member for the single mode optical fibers. There are three single mode optical fibers in all, which are indicated by the solid lines. They are arranged with each other at 120-degree intervals, as shown in the cross section orthogonal to the axis (see FIG. 17B). These single mode optical fibers are fixed axially at positions indicated by the symbol G1-G1 to fixing wires (see the left cross section G1-G1 of FIG. 17B). Note that at the cross-section position H1-H1, the single mode optical fibers are free from being restrained (see the right cross section H1-H1 of FIG. 17B). The fixing wires are helically wound co-cylindrically at pitches Lp, and their contour forms the outer envelope of the fixing wires. Further, a steering wire is disposed along the center axis to move the single mode optical fibers to a desired site. In this example, external blood pressure is transferred from the single mode optical fiber fixing positions to the single mode optical fibers via the fixing wires. Note that a structural member (the fixing wires), i.e., a protective layer, for transferring pressure of the object under measurement is provided at the outer circumferential portion of the probe. In other words, FIGS. 17A-17B illustrate that one embodiment of the structural member is formed of triple helical fixing wires co-cylindrically arranged separated from each other at 120-degree center angle intervals and is fixed, on the co-cylindrical envelope of the wires, to an outer surface of the single mode optical fibers.

REFERENCE NUMERALS

1: catheter (blood vessel insertable pressure distribution measurement device);
2: J-tip;
3, 13: single mode optical fiber (SM fiber);
4: structural member;
5: outer layer;
6: steering handle;
7: multiple SM fibers;
8: measurement unit;
9: data memory unit;
10: analyzer/display unit;
11: stainless steel frame;
12: glue;
14: image fiber;
15: tomographic image measurement fiber (OCT measurement fiber);
16: wire layer; and
20: pulse detection fiber.

The invention claimed is:
1. A fiber optic diagnostic sensor system comprising:
a blood vessel insertable pressure distribution measurement device to be inserted into a blood vessel to measure distributions of temperature and pressure of an object to be measured along a predetermined site, the measurement device having:
an outer layer deformable by external pressure and preventing the to-be-measured object from entering into an inside of the outer layer, the outer layer possessing an inner surface;
a single mode optical fiber deformable by temperature and strain, the single mode optical fiber possessing an outer surface; and
a frame structural member that intermittently contacts the inner surface of the outer layer and is intermittently fixed to the outer surface of the single mode optical fiber to convert continuously the pressure applied to the outer layer, and to produce a force causing a stretching strain in the optical fiber to transfer the force to the optical fiber,
a measurement unit emitting laser light into the single mode optical fiber resulting in scattered light, the measurement unit comprising a light detector that continuously detects a scattered light frequency shift produced in the single mode optical fiber, the scattered light frequency shift being detected by the light detector detecting a Rayleigh frequency shift in the scattered light and a Brillouin frequency shift in the scattered light, and the measurement unit calculating a blood pressure at a given position of the single mode optical fiber from a temperature change and a strain change of the optical fiber that are calculated from the detected scattered light frequency shift including the Rayleigh frequency shift and the Brillouin frequency shift;
a memory unit storing the blood pressure calculated by the measurement unit; and an analyzed/display unit performing an analysis and display on the basis of the calculated blood pressure stored in the memory unit.

2. The fiber optic diagnostic sensor system of claim 1, wherein the blood vessel insertable pressure distribution measurement device is equipped with at least two single mode optical fibers, one of the optical fibers disposed so as not to be subjected to pressure transferred from outer layer so that the one optical fiber produces strain by a temperature change; and the light detector of the measurement unit detects frequency shifts in Rayleigh scattered light in both of the two single mode optical fibers so that the calculating of the blood pressure by the measurement unit includes the frequency shifts in Rayleigh scattered light in both of the two single mode optical fibers.

3. The fiber optic diagnostic sensor system of claim 1, wherein the single mode optical fiber has a reflection device at the distal end of the optical fiber.

4. The fiber optic diagnostic sensor system of claim 1, further comprising: a pulse detection fiber to be wound around a portion of an arm to detect heartbeat, wherein the measurement unit of the sensor system detects a heartbeat signal by the pulse detection fiber and controls timing of detecting a frequency shift in the scattered light in synchronism with the detected heartbeat signal.

5. A blood vessel insertable pressure distribution measurement device to be inserted in a blood vessel to measure distributions of temperature and pressure of an object to be measured along a predetermined site, the measurement device comprising:
an outer layer deformable by external pressure and preventing the to-be-measured object from entering into an inside of the outer layer;
a single mode optical fiber deformable by temperature and strain; and
a frame structural member that intermittently contacts the inner surface of the outer layer at spaced apart locations along a length of the outer layer in an axial direction and is intermittently fixed to the outer surface of the single mode optical fiber at spaced apart locations along a length of the single mode optical fiber in the axial direction to convert continuously the pressure applied to the outer layer, and to produce a force causing a stretching strain in the optical fiber to transfer the force to the optical fiber.

6. The blood vessel insertable pressure distribution measurement device of claim 5, wherein the frame structural member has a hollow space, and is fixed to the single mode optical fiber at a center axis of the frame structural member and in contact with the outer layer at outer circumferential potions of the frame structural member.

7. The blood vessel insertable pressure distribution measurement device of claim 5, wherein the frame structural member is formed of:
three single mode optical fibers deformable by temperature and strain, the three single mode optical fibers being separated at 120-degree center angle intervals from each other, and
triple helical fixing wires that intermittently contact the inner surface of the outer layer and are intermittently fixed to the outer surface of the three single mode optical fibers to convert continuously the pressure applied to the outer layer, and to produce a force causing a stretching strain in each optical fiber to transfer the force to each optical fiber,
wherein the triple helical fixing wires are co-cylindrically arranged separated from each other at 120-degree center angle intervals.

* * * * *